(12) United States Patent
Yarnitsky et al.

(10) Patent No.: US 11,730,414 B2
(45) Date of Patent: Aug. 22, 2023

(54) AUTOMATIC PATTERN ACQUISITION

(71) Applicant: BIOSENSE WEBSTER (ISRAEL) LTD., Yokneam (IL)

(72) Inventors: Jonathan Yarnitsky, Haifa (IL); Elad Nakar, Haifa (IL); Lior Greenbaum, Zoran (IL); Goren Cohn, Haifa (IL); Amiram Ben Dor, Haifa (IL)

(73) Assignee: Biosense Webster (Israel) Ltd., Yokeam (IL)

( * ) Notice: Subject to any disclaimer, the term of this patent is extended or adjusted under 35 U.S.C. 154(b) by 194 days.

(21) Appl. No.: 17/109,498

(22) Filed: Dec. 2, 2020

(65) Prior Publication Data

US 2021/0219904 A1    Jul. 22, 2021

Related U.S. Application Data

(60) Provisional application No. 62/963,710, filed on Jan. 21, 2020.

(51) Int. Cl.
| | |
|---|---|
| *A61B 5/35* | (2021.01) |
| *A61B 5/339* | (2021.01) |
| *A61B 5/36* | (2021.01) |
| *A61B 5/367* | (2021.01) |
| *A61B 5/287* | (2021.01) |
| *A61B 5/06* | (2006.01) |

(52) U.S. Cl.
CPC ............... *A61B 5/35* (2021.01); *A61B 5/339* (2021.01); *A61B 5/36* (2021.01); *A61B 5/367* (2021.01); *A61B 5/062* (2013.01); *A61B 5/287* (2021.01)

(58) Field of Classification Search
CPC .................................. A61B 5/35; A61B 5/339
USPC ........................................................ 600/516
See application file for complete search history.

(56) References Cited

U.S. PATENT DOCUMENTS

| | | | |
|---|---|---|---|
| 8,452,404 B1 * | 5/2013 | Fischell | A61B 5/352 607/9 |
| 2002/0026220 A1 | 2/2002 | Groenewegen | |
| 2002/0193695 A1 | 12/2002 | Koyrakh | |

(Continued)

FOREIGN PATENT DOCUMENTS

EP    1804913 B1    7/2011

OTHER PUBLICATIONS

European Search Report for corresponding EPA No. 21152433.5 dated Jun. 24, 2021.

*Primary Examiner* — Nicole F Lavert

(57) ABSTRACT

In one embodiment, a medical system includes respective electrodes for application to a body of a subject and to output a set of respective activation signals in response to electrical activity of a heart of the subject captured over a sequence of heartbeat intervals, and a processor to classify a first heartbeat interval of the set of activation signals as a first morphological template, compute a measure of similarity between a second heartbeat interval of the set of activation signals and the first morphological template, group the second heartbeat interval of the set of activation signals in a first morphological group with the first morphological template responsively to the measure exceeding a predefined threshold, and classify the second heartbeat interval of the set of activation signals as a second morphological template responsively to the measure not exceeding the predefined threshold, and repeat the above, mutatis mutandis, for subsequent heartbeat intervals.

14 Claims, 9 Drawing Sheets

(56) References Cited

U.S. PATENT DOCUMENTS

| | | |
|---|---|---|
| 2005/0137485 A1 | 6/2005 | Cao |
| 2008/0234770 A1 | 9/2008 | Kim |
| 2009/0275850 A1 | 11/2009 | Mehendale |
| 2010/0280400 A1 | 11/2010 | Ettori |
| 2011/0166613 A1 | 7/2011 | Li |
| 2011/0238127 A1 | 9/2011 | Conley |
| 2012/0108994 A1 | 5/2012 | Patel |
| 2016/0213311 A1 | 7/2016 | Zhang |
| 2016/0213941 A1 * | 7/2016 | Zhang .................. A61N 1/3702 |

* cited by examiner

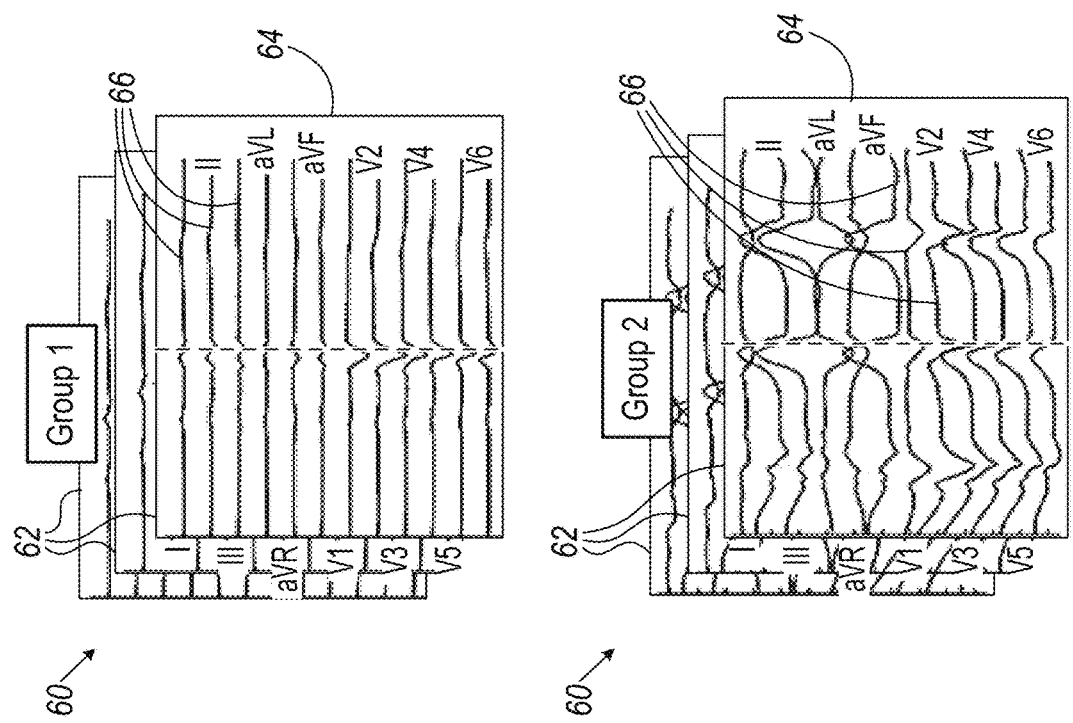
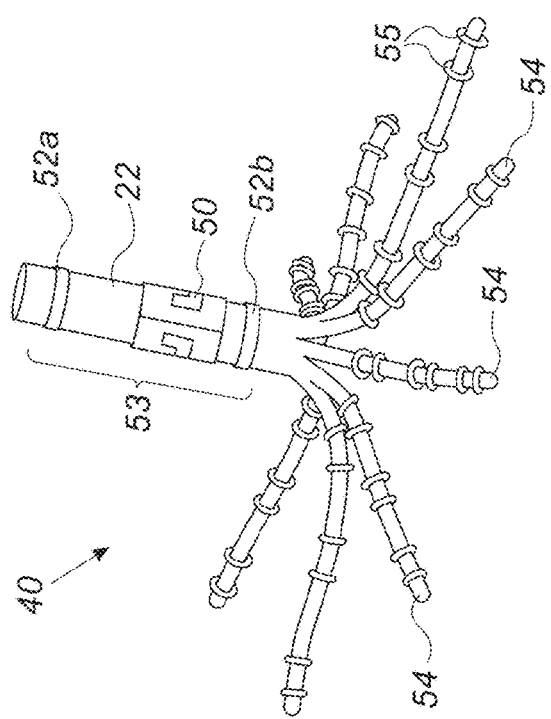
FIG. 3
FIG. 2

FIG. 11

AUTOMATIC PATTERN ACQUISITION

CROSS-REFERENCE TO RELATED APPLICATIONS

The present application claims benefit of U.S. Provisional Patent Application No. 62/963,710 filed 21 Jan. 2020, the disclosure of which is hereby incorporated herein by reference.

FIELD OF THE INVENTION

The present invention relates to medical devices, and in particular but not exclusively to, measuring electrical activation.

BACKGROUND

The process of electrocardiography (ECG) records electrical activity of the heart over a time period using electrodes applied to the skin of a living subject. The electrodes detect electrical charges on the skin that arise from the heart's electrophysiologic pattern of depolarizing and repolarizing during each heartbeat.

Electrocardiography may be performed to detect cardiac problems such as arrhythmia of the heart as well as to monitor improvement in the condition of the heart after corrective procedures, for example, but not limited to, ablation therapy.

A standard electrocardiograph may include connections to ten electrodes which are applied to the skin of the living subject including on the subject's limbs and on the chest. The electrical potential of the heart is then measured using the ten electrodes and is recorded over a time period. In this manner, the overall magnitude and direction of the heart's electrical depolarization is captured at each moment throughout the cardiac cycle. A graph of voltage versus time may be produced yielding an electrocardiogram.

During a medical procedure such as cardiac ablation, there are typically simultaneous streams of real-time data that an operator (e.g., a physician) monitors while performing the procedure. For example, while using an intracardiac catheter to perform an ablation on intracardiac tissue, the operator may want to keep track of real-time electrophysiological (EP) data such as ECG data and ancillary data such as locations of the catheter's distal tip and ablation energy being delivered to the heart tissue.

US Patent Publication No. 2002/0026220 to Groenewegen, et al., describes classification and localization of arrhythmias. More specifically, a system and method are provided for developing a database of body surface ECG P wave maps for classification and localization of left-sided atrial arrhythmias. The invention includes generating and receiving P wave data in a subject by left atrial pacing or receiving P wave data in a subject during spontaneously occurring or induced left atrial arrhythmias; computing (e.g. potential or integral) maps of the P wave data; classifying the maps specific to a left atrial ectopic origin; verifying the classification procedure; averaging the classified maps into mean maps; and storing and accessing the mean maps in the database. The mean maps of the P wave data in the database can be used to automatically classify and localize P wave data from a patient obtained during a left atrial arrhythmia such as atrial tachycardia, focal atrial fibrillation or orthodromic atrioventricular reentrant tachycardia.

US Patent Publication No. 2002/0193695 to Koyrakh, et al., describes a method of generating a template in an implantable medical device for implantation within a patient, and a processor readable medium for performing the method, that includes generating a template from collected events corresponding to the patient, delaying the generation of the template for a first predetermined time period in response to the template not being generated within a predetermined number of collected events, determining whether the template is valid, and monitoring the template to determine whether the template is an accurate representation of the patient.

US Patent Publication No. 2010/0280400 to Ettori, et al., describes a cardiac rhythm management system, which can be used to detect episode beats associated with cardiac events in a subject's body. These events may be monitored and depolarization morphology information can be derived for candidate arrhythmic beats in an arrhythmia episode. An arrhythmic beat morphology template may be formed from selecting at least one of the candidate arrhythmic beats based upon user's labeling according to specific morphologies of one or more candidate episodes. Methods of use are also presented.

US Patent Publication No. 2011/0238127 to Conley, et al., describes systems, devices, structures, and methods to present a visual display based on data from an implantable medical device. The display includes a chart showing the frequency of a detected type of arrhythmia over a predetermined period of time.

US Patent Publication No. 2008/0234770 to Kim, et al., describes a method and system for generating a snapshot representative of one beat of a patient's normal cardiac rhythm. Cardiac rate channel signals and shock channel signals are sensed. A fiducial point is determined for a predefined number of the cardiac rate channel signals. A predefined number of the shock channel signals are aligned using the fiducial point. A template is generated using the aligned shock channel signals, whereby the template is representative of one of the patient's normal supraventricular conducted cardiac beats. The template is updated on a periodic basis.

US Patent Publication 2005/0137485 of Cao, et al., describes an implantable medical device and associated method for automatically generating morphology templates during fast cardiac rhythms, confirming a provisional template as a confirmed template, and using the confirmed template to classify subsequent detected arrhythmias. A provisional supraventricular tachycardia (SVT) template may be created during a fast ventricular rate and activated as a confirmed SVT template upon verification that the fast rate was due to an SVT. The confirmed SVT template may be used to discriminate SVT from ventricular tachycardia or ventricular fibrillation.

SUMMARY

There is provided in accordance with an embodiment of the present disclosure, a medical system including respective electrodes configured for application to a body of a subject and configured to output a set of respective activation signals in response to electrical activity of a heart of the subject captured over a sequence of heartbeat intervals, and a processor configured to classify a first heartbeat interval of the set of activation signals as a first morphological template, for a second heartbeat interval following the first heartbeat interval compute a measure of similarity between the second heartbeat interval of the set of activation signals and the first morphological template, group the second heartbeat interval of the set of activation signals in a first morphological group with the first morphological template responsively to the measure of similarity exceeding a predefined threshold, and classify the second heartbeat interval of the set of activation signals as a second morphological template responsively to the measure of similarity not exceeding the predefined threshold, and for a subsequent heartbeat interval compute a measure of similarity between the subsequent heartbeat interval of the set of activation signals and at least one of a plurality of previously assigned morphological templates of respective morphological groups, group the subsequent heartbeat interval of the set of activation signals in one of the morphological groups of one of the previously assigned morphological templates responsively to the measure of similarity with the one previously assigned morphological template exceeding a predefined threshold, and classify the subsequent heartbeat interval of the set of activation signals as another morphological template responsively to the measure of similarity with the previously assigned morphological templates not exceeding the predefined threshold.

Further in accordance with an embodiment of the present disclosure the processor is configured to find a new morphological template for one of the morphological groups responsively to a number of heartbeat intervals of the set of activation signals in the one morphological group exceeding a given threshold size.

Still further in accordance with an embodiment of the present disclosure the processor is configured to select one of the heartbeat intervals of the set of activation signals most similar to other ones of the heartbeat intervals of the set of activation signals in the one morphological group as the new morphological template.

Additionally, in accordance with an embodiment of the present disclosure, the system includes a display, wherein the processor is configured to render to the display a user interface screen including respective ones of the morphological templates and indications of respective relative numbers of heartbeat intervals of the set of activation signals in respective ones of the morphological groups.

Moreover, in accordance with an embodiment of the present disclosure the indication includes a histogram indicating the respective relative numbers of the heartbeat intervals of the set of activation signals in the respective ones of the morphological groups.

Further in accordance with an embodiment of the present disclosure the indication includes a count and/or an activation percentage and/or an occurrence rate of the heartbeat intervals of the set of activation signals in the respective ones of the morphological groups.

Still further in accordance with an embodiment of the present disclosure the processor is configured to order the respective ones of the morphological templates in the user interface screen any one or more of the following a count of the heartbeat intervals of the set of activation signals in the respective ones of the morphological groups, an activation percentage or an occurrence rate of the heartbeat intervals of the set of activation signals in the respective ones of the morphological groups, an earliest activation of the heartbeat intervals of the set of activation signals in the respective ones of the morphological groups, or a latest activation of the heartbeat intervals of the set of activation signals in the respective ones of the morphological groups.

Additionally, in accordance with an embodiment of the present disclosure the processor is configured to select the respective ones of the morphological templates included in the user interface screen from the morphological templates any one or more of the following filters a minimum count of the heartbeat intervals of the set of activation signals in the respective ones of the morphological groups, a minimum activation percentage or an occurrence rate of the heartbeat intervals of the set of activation signals in the respective ones of the morphological groups, a last activation of the heartbeat intervals of the set of activation signals in the respective ones of the morphological groups, a minimum consecutive sequence of heartbeat intervals in a same one of the morphological groups.

Moreover in accordance with an embodiment of the present disclosure the processor is configured to receive a user selection assigning a favorite of the morphological templates, the processor being configured to render the favorite in the user interface screen even if the favorite is not selected the one or more filters.

Further in accordance with an embodiment of the present disclosure the processor is configured to separately track first respective numbers of heartbeat intervals of the set of activation signals added to the respective morphological groups prior to, and during, a verification period, and second respective numbers of heartbeat intervals of the set of activation signals added to the respective morphological groups during the verification period, and the processor is configured to render to the display the user interface screen, which simultaneously includes indications of the first respective numbers and the second respective numbers of heartbeat intervals added to the respective morphological groups.

Still further in accordance with an embodiment of the present disclosure the processor is configured to emphasize a new morphological template created during the verification period.

Additionally, in accordance with an embodiment of the present disclosure the processor is configured to render the user interface screen including a graph of cardiac cycle length against time, the graph indicating when a morphology of a selected one of the morphological groups was active.

Moreover, in accordance with an embodiment of the present disclosure, the system includes a display, wherein the processor is configured to compute respective measures of similarity between a pacing induced heartbeat interval of the set of activation signals and respective ones of the previously assigned morphological templates of respective morphological groups, and render to the display a user interface screen including indications of the respective measures of similarity between the pacing induced heartbeat interval of the set of activation signals and the respective previously assigned morphological templates of the respective morphological groups.

Further in accordance with an embodiment of the present disclosure the processor is configured to render to the display the user interface screen including the respective previously assigned morphological templates and the indications of the respective measures of similarity between the pacing induced heartbeat interval of the set of activation signals and the respective previously assigned morphological templates of the respective morphological groups.

There is also provided in accordance with another embodiment of the present disclosure, a medical method including applying respective electrodes to a body of a subject, outputting by the electrodes a set of respective activation signals in response to electrical activity of a heart of the subject captured over a sequence of heartbeat intervals, classifying a first heartbeat interval of the set of activation signals as a first morphological template, for a second heartbeat interval following the first heartbeat interval computing a measure of similarity between the second heartbeat interval of the set of activation signals and the first morphological template, grouping the second heartbeat interval of the set of activation signals in a first morphological group with the first morphological template responsively to the measure of similarity exceeding a predefined threshold, and classifying the second heartbeat interval of the set of activation signals as a second morphological template responsively to the measure of similarity not exceeding the predefined threshold, and for a subsequent heartbeat interval computing a measure of similarity between the subsequent heartbeat interval of the set of activation signals and at least one of a plurality of previously assigned morphological templates of respective morphological groups, grouping the subsequent heartbeat interval of the set of activation signals in one of the morphological groups of one of the previously assigned morphological templates responsively to the measure of similarity with the one previously assigned morphological template exceeding a predefined threshold, and classifying the subsequent heartbeat interval of the set of activation signals as another morphological template responsively to the measure of similarity with the previously assigned morphological templates not exceeding the predefined threshold.

Still further in accordance with an embodiment of the present disclosure, the method includes finding a new morphological template for one of the morphological groups responsively to a number of heartbeat intervals of the set of activation signals in the one morphological group exceeding a given threshold size.

Additionally, in accordance with an embodiment of the present disclosure, the method includes selecting one of the heartbeat intervals of the set of activation signals most similar to other ones of the heartbeat intervals of the set of activation signals in the one morphological group as the new morphological template.

Moreover, in accordance with an embodiment of the present disclosure, the method includes rendering to a display a user interface screen including respective ones of the morphological templates and indications of respective relative numbers of heartbeat intervals of the set of activation signals in respective ones of the morphological groups.

Further in accordance with an embodiment of the present disclosure the indication includes a histogram indicating the respective relative numbers of the heartbeat intervals of the set of activation signals in the respective ones of the morphological groups.

Still further in accordance with an embodiment of the present disclosure the indication includes a count and/or an activation percentage and/or an occurrence rate of the heartbeat intervals of the set of activation signals in the respective ones of the morphological groups.

Additionally, in accordance with an embodiment of the present disclosure, the method includes ordering the respective ones of the morphological templates in the user interface screen any one or more of the following a count of the heartbeat intervals of the set of activation signals in the respective ones of the morphological groups, an activation percentage or an occurrence rate of the heartbeat intervals of the set of activation signals in the respective ones of the morphological groups, an earliest activation of the heartbeat intervals of the set of activation signals in the respective ones of the morphological groups, or a latest activation of the heartbeat intervals of the set of activation signals in the respective ones of the morphological groups.

Moreover, in accordance with an embodiment of the present disclosure, the method includes selecting the respective ones of the morphological templates included in the user interface screen from the morphological templates any one or more of the following filters a minimum count of the heartbeat intervals of the set of activation signals in the respective ones of the morphological groups, a minimum activation percentage or an occurrence rate of the heartbeat intervals of the set of activation signals in the respective ones of the morphological groups, a last activation of the heartbeat intervals of the set of activation signals in the respective ones of the morphological groups, a minimum consecutive sequence of heartbeat intervals in a same one of the morphological groups.

Further in accordance with an embodiment of the present disclosure, the method includes receiving a user selection assigning a favorite of the morphological templates, and rendering the favorite in the user interface screen even if the favorite is not selected the one or more filters.

Still further in accordance with an embodiment of the present disclosure, the method includes separately tracking first respective numbers of heartbeat intervals of the set of activation signals added to the respective morphological groups prior to, and during, a verification period, and second respective numbers of heartbeat intervals of the set of activation signals added to the respective morphological groups during the verification period, and wherein the rendering includes rendering to the display the user interface screen, which simultaneously includes indications of the first respective numbers and the second respective numbers of heartbeat intervals added to the respective morphological groups.

Additionally, in accordance with an embodiment of the present disclosure, the method includes emphasizing a new morphological template created during the verification period.

Moreover, in accordance with an embodiment of the present disclosure the rendering includes rendering the user interface screen including a graph of cardiac cycle length against time, the graph indicating when a morphology of a selected one of the morphological groups was active.

Further in accordance with an embodiment of the present disclosure, the method includes computing respective measures of similarity between a pacing induced heartbeat interval of the set of activation signals and respective ones of the previously assigned morphological templates of respective morphological groups, and rendering to a display a user interface screen including indications of the respective measures of similarity between the pacing induced heartbeat interval of the set of activation signals and the respective previously assigned morphological templates of the respective morphological groups.

Still further in accordance with an embodiment of the present disclosure the rendering includes rendering to the display the user interface screen including the respective previously assigned morphological templates and the indications of the respective measures of similarity between the pacing induced heartbeat interval of the set of activation signals and the respective previously assigned morphological templates of the respective morphological groups.

BRIEF DESCRIPTION OF THE DRAWINGS

The present invention will be understood from the following detailed description, taken in conjunction with the drawings in which:

FIG. 2 is a schematic view of a catheter for use in the system of FIG. 1;

FIG. 3 is a schematic view of morphological groups for use in the system of FIG. 1;

FIG. 11 is a schematic view of a pacing user interface screen generated by the system of FIG. 1.

DESCRIPTION OF EXAMPLE EMBODIMENTS

Overview

Figure 1:
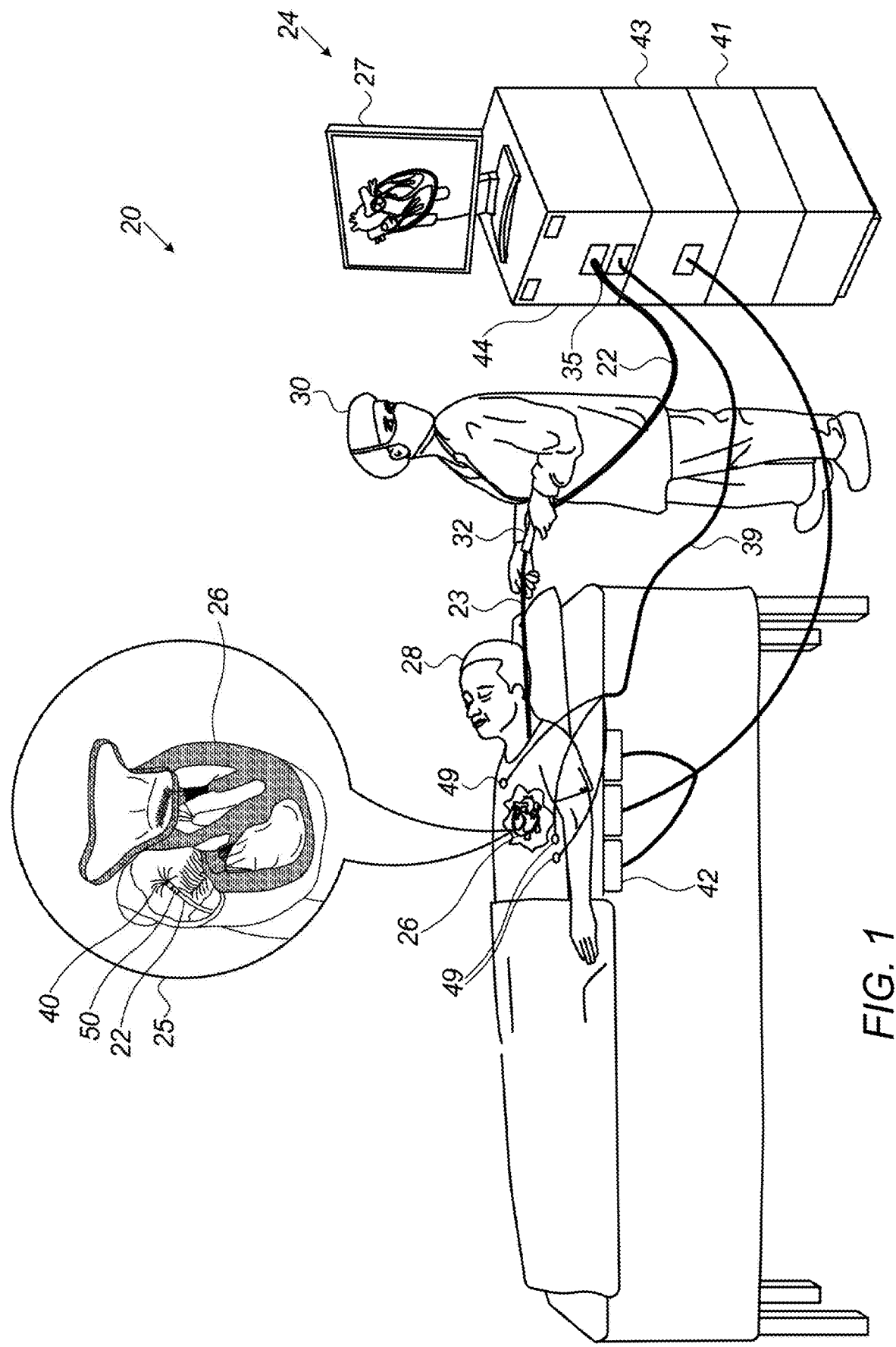
FIG. 1 is a schematic view of a medical procedure system constructed and operative in accordance with an embodiment of the present invention.

In analyzing electrocardiogram (ECG) signals or intracardiac (IC) electrograms (IEGM) for different types of arrhythmia, a physician may visually inspect graphs of the signals, and decide from the inspection what type and when the arrhythmia occurred. This sort of visual inspection is time-consuming, and is also open to potential error. Correct identification of arrhythmias is particularly critical during cardiac procedures such as ablation therapy wherein ablations may be targeted according to the different arrhythmias present.

In some systems, due to the large amount of data produced during a procedure, for example, ablation and ECG and/or IEGM data, the physician may set different filters for acquiring the relevant electro-anatomical data to include in the heart conduction map. For example, although the ECG and/or IEGM data may be indicative of many different arrhythmias, the physician may set filters to detect one or more of the different types of arrhythmia based on pattern matching. As the heart rhythm may change while the procedure continues, for example, due to corrective measures being performed, the physician may change the filters during the procedure. Having to allocate a specific pattern, representative of the mapped arrhythmia, out of the entire set of activations may be difficult, time-consuming, and also prone to error.

Embodiments of the present invention, provide automatic pattern acquisition to provide a burden analysis of the activity in the mapped chamber, and to automate the pattern acquisition process for both body surface (BS) and intracardiac (IC) reference signals without requiring the physician to preselect specific patterns. The term "pattern" as used in the specification and claims, is defined as a set of respective heartbeat activation signals from respective ECG and/or IEGM channels for a single heartbeat interval. The term "group" as used in the specification and claims, is defined as a set of patterns with similar morphology with each group being represented by a morphological template which may be one selected pattern from that group.

Automation of acquisition reduces manual intervention of the operator, and potentially reduces procedure time and improves efficiency. The system groups recorded heartbeats into groups of similar morphology, while a set of filters allows the physician to select which of the groups is of most interest. The automated process allows classification of all heartbeats, and provides the data to easily identify the prominent activations for mapping as well as for tracking of post ablation treatment success.

In some embodiments, a first incoming heartbeat set (pattern) forms the first morphological template of a first morphological group. A second incoming heartbeat set (pattern) is compared to the first morphological template. If there is a suitable match, the second heartbeat set (pattern) is added to the first morphological group. If there is not a suitable match, the second heartbeat set forms the morphological template of another morphological group. Subsequent incoming heartbeat sets (patterns) are compared to one or more existing morphological templates and if there is a match they are added to the matching morphological group and if not, a new morphological group is created, and so on. The morphological templates and groups are formed dynamically based on the matching between incoming beats and existing morphological templates.

The algorithm utilizes an optimization process, which selects the best representing heartbeat set for each group as the group's morphological template. An optimized template contributes to higher correlation values with similar activations while mapping, elevating the pattern matching capabilities.

Acquisition of BS based patterns, for ventricle mappings, can be achieved as soon as the patient is stable and connected to the BS patches. Automatic acquisition can make use of the procedure preparation time to collect patterns and classify activations so to reduce mapping time, eliminate the effect of mechanically induced beats and provide required statistics of burden activity.

In some embodiment, a user interface screen may be rendered showing at least some of the created templates, and statistics indicating the activation count and/or activation percentage associated with each of the morphological groups of the displayed morphological templates. A histogram may also be used to indicate the activation count and/or activation percentage associated with the morphological groups of the morphological templates. The user interface screen may also include a cycle length graph of cycle length against time. Displayed morphological templates may be selected by the physician and the time of activation of the heartbeats of the selected morphology may be shown on the cycle length graph. Filters may be set by the physician to determine which morphological templates and associated data should be shown on the user interface screen. Additional settings may be set to determine an order of the data on the user interface screen.

In some embodiments, a processor separately tracks: first numbers of heartbeat intervals added to respective morphological groups prior to a verification period (e.g., after ablation has been performed); and second numbers of heartbeat intervals added to the respective morphological groups only during the verification period. The processor renders the user interface screen, which simultaneously includes indications of the first numbers and the second numbers of heartbeat intervals added to the respective morphological groups thereby allowing easy verification of the effectiveness of treatment such as ablation, for example, to see if an arrhythmia present prior to ablation is still present after ablation during the verification period.

The activation count of heartbeat intervals in one or more of the respective morphological groups may be too low to successfully generate a meaningful electro-anatomical map, e.g., a local activation time (LAT) map, for any of the low count morphological groups. However, the physician may want to identify the source of the arrhythmia associated with any one of the low count groups and perform an ablation at the source of the arrhythmia associated with that low count group. Pacing may be used to help identify the source of the arrhythmia.

In some embodiments, although the pacing induced beats are generally not added to any of the morphological groups, pacing induced beats are compared to at least some (or all) of the morphological templates to determine measures of similarity with the respective morphological templates. The measures of similarity may be displayed in real-time so that the physician may determine the source of arrhythmia based on the measures of similarity. For example, the catheter is moved around a chamber of the heart, and when the catheter is disposed at a certain location in the chamber of the heart, the measure of similarity to one of the morphological templates is greater than 90% (for example), which provides a good indication that the catheter is disposed close to the source of the arrhythmia associated with that morphological template. The physician may then decide to ablate at that location.

System Description

Reference is now made to FIG. 1, which is a schematic view of a medical procedure system 20 constructed and operative in accordance with an embodiment of the present invention. Reference is also made to FIG. 2, which is a schematic view of a catheter 40 for use in the system 20 of FIG. 1.

The medical procedure system 20 is used to determine the position of the catheter 40, seen in an inset 25 of FIG. 1 and in more detail in FIG. 2. The catheter 40 is a probe which includes a shaft 22 and a plurality of deflectable arms 54 (only some labeled for the sake of simplicity) for inserting into a body-part (e.g., chamber of a heart 26) of a living subject. The deflectable arms 54 have respective proximal ends connected to the distal end of the shaft 22.

The catheter 40 includes a position sensor 53 disposed on the shaft 22 in a predefined spatial relation to the proximal ends of the deflectable arms 54. The position sensor 53 may include a magnetic sensor 50 and/or at least one shaft electrode 52. The magnetic sensor 50 may include at least one coil, for example, but not limited to, a dual-axis or a triple axis coil arrangement to provide position data for location and orientation including roll. The catheter 40 includes multiple electrodes 55 (only some are labeled in FIG. 2 for the sake of simplicity) disposed at different, respective locations along each of the deflectable arms 54. Typically, the catheter 40 may be used for mapping electrical activity in a heart of the living subject using the electrodes 55, or for performing any other suitable function in a body-part of a living subject, for example, but not limited to, reversible and/or irreversible electroporation and/or RF ablation.

The medical procedure system 20 may determine a position and orientation of the shaft 22 of the catheter 40 based on signals provided by the magnetic sensor 50 and/or the shaft electrodes 52 (proximal-electrode 52a and distal-electrode 52b) fitted on the shaft 22, on either side of the magnetic sensor 50. The proximal-electrode 52a, the distal-electrode 52b, the magnetic sensor 50 and at least some of the electrodes 55 are connected by wires running through the shaft 22 via a catheter connector 35 to various driver circuitries in a console 24. In some embodiments, at least two of the electrodes 55 of each of the deflectable arms 54, the shaft electrodes 52, and the magnetic sensor 50 are connected to the driver circuitries in the console 24 via the catheter connector 35. In some embodiments, the distal-electrode 52b and/or the proximal electrode 52a may be omitted.

The illustration shown in FIG. 2 is chosen purely for the sake of conceptual clarity. Other configurations of shaft electrodes 52 and electrodes 55 are possible. Additional functionalities may be included in the position sensor 53. Elements which are not relevant to the disclosed embodiments of the invention, such as irrigation ports, are omitted for the sake of clarity.

A physician 30 navigates the catheter 40 to a target location in a body part (e.g., the heart 26) of a patient 28 by manipulating the shaft 22 using a manipulator 32 near the proximal end of the catheter 40 and/or deflection from a sheath 23. The catheter 40 is inserted through the sheath 23, with the deflectable arms 54 gathered together, and only after the catheter 40 is retracted from the sheath 23, the deflectable arms 54 are able to spread and regain their intended functional shape. By containing deflectable arms 54 together, the sheath 23 also serves to minimize vascular trauma on its way to the target location.

Console 24 comprises processing circuitry 41, typically a general-purpose computer and a suitable front end and interface circuits 44 for generating signals in, and/or receiving signals from, body surface electrodes 49 which are attached by wires running through a cable 39 to the chest and to the back, or any other suitable skin surface, of the patient 28.

Console 24 further comprises a magnetic-sensing subsystem. The patient 28 is placed in a magnetic field generated by a pad containing at least one magnetic field radiator 42, which is driven by a unit 43 disposed in the console 24. The magnetic field radiator(s) 42 is configured to transmit alternating magnetic fields into a region where the body-part (e.g., the heart 26) is located. The magnetic fields generated by the magnetic field radiator(s) 42 generate direction signals in the magnetic sensor 50. The magnetic sensor 50 is configured to detect at least part of the transmitted alternating magnetic fields and provide the direction signals as corresponding electrical inputs to the processing circuitry 41.

In some embodiments, the processing circuitry 41 uses the position-signals received from the shaft electrodes 52, the magnetic sensor 50 and the electrodes 55 to estimate a position of the catheter 40 inside an organ, such as inside a cardiac chamber. In some embodiments, the processing circuitry 41 correlates the position signals received from the electrodes 52, 55 with previously acquired magnetic location-calibrated position signals, to estimate the position of the catheter 40 inside the organ. The position coordinates of the shaft electrodes 52 and the electrodes 55 may be determined by the processing circuitry 41 based on, among other inputs, measured impedances, or on proportions of currents distribution, between the electrodes 52, 55 and the body surface electrodes 49. The console 24 drives a display 27, which shows the distal end of the catheter 40 inside the heart 26.

The method of position sensing using current distribution measurements and/or external magnetic fields is implemented in various medical applications, for example, in the Carto® system, produced by Biosense Webster Inc. (Irvine, Calif.), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publication Nos. 2002/0065455 A1, 2003/0120150 A1 and 2004/0068178 A1.

The Carto®3 system applies an Active Current Location (ACL) impedance-based position-tracking method. In some embodiments, using the ACL method, the processing circuitry 41 is configured to create a mapping (e.g., current-position matrix (CPM)) between indications of electrical impedance and positions in a magnetic coordinate frame of the magnetic field radiator(s) 42. The processing circuitry 41 estimates the positions of the shaft electrodes 52 and the electrodes 55 by performing a lookup in the CPM.

Other methods of determining the location of the distal end of the catheter may be used, for example, based on ultrasonic transducers and receivers, using imaging techniques such as ultrasound or MRI or CT scans which may include disposing radiopaque tags on the catheter 40.

Processing circuitry 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

FIG. 1 shows only elements related to the disclosed techniques, for the sake of simplicity and clarity. The system 20 typically comprises additional modules and elements that are not directly related to the disclosed techniques, and thus are intentionally omitted from FIG. 1 and from the corresponding description.

The catheter 40 described above includes eight deflectable arms 54 with six electrodes 55 per arm 54. Any suitable catheter may be used instead of the catheter 40, for example, a catheter with a different number of flexible arms and/or electrodes per arm, or a different probe shape such as a balloon catheter or basket catheter or a lasso catheter, by way of example only.

The medical procedure system 20 may also perform electroporation or RF ablation (or other ablation technique) of heart tissue using any suitable catheter, for example using the catheter 40 or a different catheter and any suitable ablation method. The console 24 may include a signal generator 34 configured to generate an electrical signal to be applied by an electrode or electrodes of a catheter connected to the console 24, (and optionally one or more of the body surface electrodes 49), to perform electroporation or RF ablation of a myocardium of the heart 26. The console 24 may include a pump (not shown), which pumps irrigation fluid into an irrigation channel to a distal end of a catheter performing RF ablation. The catheter performing the RF ablation may also include temperature sensors (not shown) which are used to measure a temperature of the myocardium during RF ablation and regulate an ablation power and/or an irrigation rate of the pumping of the irrigation fluid according to the measured temperature.

Reference is now made to FIG. 3, which is a schematic view of morphological groups 60 for use in the system 20 of FIG. 1. The morphological groups 60 are dynamically created during the pattern matching process described below with reference to FIG. 4. Each morphological groups 60 includes set of patterns 62 with similar morphology and each group is represented by a morphological template 64 which may be one selected pattern 62 from that group 60. Each pattern 62 includes a set of respective heartbeat activation signals 66 (only some labeled for the sake of simplicity) from respective ECG and/or IEGM channels for a single heartbeat interval. The example activation signals 66 shown in FIG. 3 are ECG signals.

Figure 4:
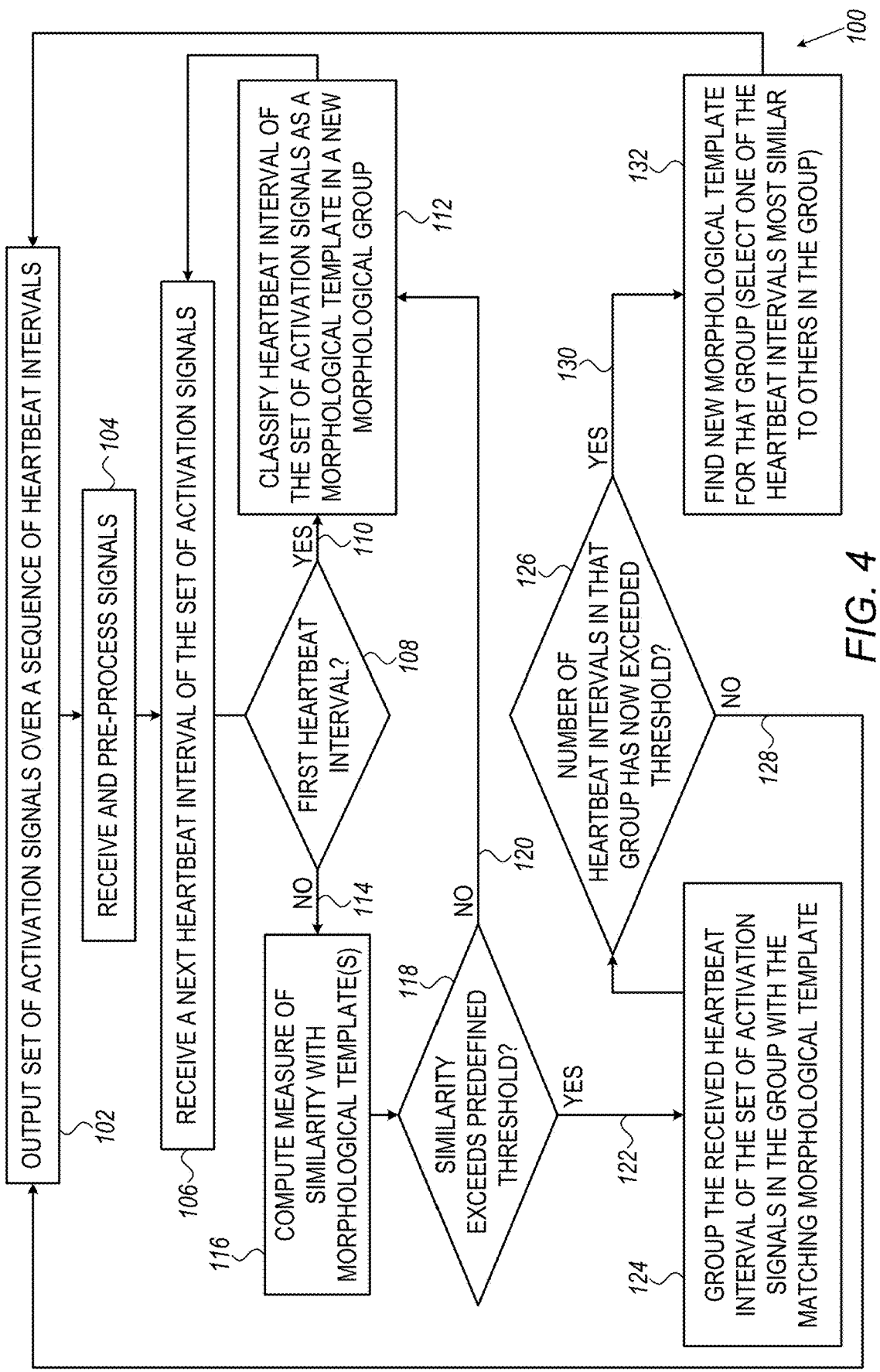
FIGS. 4-7 are flowcharts including steps in methods of operation of the system of FIG. 1.

Reference is now made to FIG. 4, which is a flowchart 100 including steps in a pattern matching method for use in the system 20 of FIG. 1. The automatic pattern matching method is typically activated by the physician 30 (FIG. 1) and may be activated as soon as the relevant data stream is available, e.g., from the body surface electrodes 49 (FIG. 1) and/or from the electrodes 55 (FIG. 2) of the catheter 40 (FIG. 2), and the reference signals are stable. The catheter 40 described with reference to FIG. 2 is an eight-spline catheter. For the automatic pattern matching method, any suitable catheter may be used such that it is placed in a stable and fixed position relative to the mapped chamber. The stability of the catheter is important in order to capture comparable and representative patterns of different arrythmias, as manifested on the intra-cardiac signals at the same location(s) for the duration of the medical procedure. In some embodiments, a linear catheter including one or more electrodes may be used and placed in the Coronary Sinus (CS).

The respective electrodes (e.g., the body surface electrodes 49 and/or the catheter electrodes) are configured for application to a body of a subject (e.g., the patient 28) and configured to output (block 102) a set of respective activation signals 66 (FIG. 3) in response to electrical activity of the heart 26 (FIG. 1) of the subject captured over a sequence of heartbeat intervals.

The processing circuitry 41 is configured to receive and pre-process (block 104) the activation signals 66. The pre-processing may include annotating the activation signals 66 to generate time stamps which identify the locations of the relevant electrical activation in the activation signals 66. The activation signals 66 are therefore divided into intervals by the time stamps with each interval representing the electrical activity associated with a heartbeat. Pre-processing of the activation signals 66 is described in more detail with reference to FIG. 5.

The processing circuitry 41 is configured to receive (block 106) a (next) heartbeat interval of the set of activation signals 66 from the electrodes (e.g., the body surface electrodes 49 and/or the catheter electrodes). At a decision block 108, the processing circuitry 41 checks if the received heartbeat interval is the first heartbeat interval. If the received heartbeat interval is the first (branch 110), the processing circuitry 41 is configured to classify (block 112) the first heartbeat interval of the set of activation signals 66 as a first morphological template 64 in a new morphological group 60 (even though there is currently only one member of the morphological group 60). If the received heartbeat interval is not the first (branch 114) (for example, it is the second or a subsequent interval), the processing circuitry 41 is configured to compute (block 116) a measure of similarity between the currently received heartbeat interval of the set of activation signals 66 and the previously assigned morphological template(s) 64. At a decision block 118, the processing circuitry 41 is configured to determine if the measure of similarity exceeds a predefined threshold. If the measure of similarity does not exceed the predefined threshold (branch 120), the processing circuitry 41 is configured to classify (block 112) the currently received heartbeat interval of the set of activation signals 66 as a new (second or subsequent) morphological template 64. If the measure of similarity does exceed the predefined threshold (branch 122), the processing circuitry 41 is configured to group (block 124) the currently received heartbeat interval of the set of activation signals 66 in the morphological group 60 with the morphological template 64 to which the currently receive heart beat interval of the set of activation signals 66 matched. For example, the second heartbeat interval of the set of the activation signals 66 may be grouped with the first morphological template 64 in the first morphological group 60. The steps of blocks 116-118 are described in more detail with reference to FIG. 6.

At a decision block 126, the processing circuitry 41 is configured to determine if a number of heartbeat intervals of the set of activation signals 66 in the morphological group 60 (e.g., the one which the currently received heart beat interval was added to) has now exceeded a given threshold size. The given threshold size may be any suitable threshold size, for example, in the range of 10-50 patterns, e.g., 20 patterns. If the number of heartbeat intervals of the set of activation signals 66 in the morphological group 60 has not currently exceeded the given threshold size (branch 128), even though it has previously, processing continues with the step of block 102 where a next pattern is processed. If the number of heartbeat intervals of the set of activation signals 66 in the morphological group 60 has now exceeded the given threshold size (branch 130), the processing circuitry 41 is configured to find (block 132) a new morphological template for that morphological group 60 from all the patterns 62 in that morphological group 60. The term "now exceeded" is defined to include where the threshold size is first exceeded, but not subsequently exceeded. Therefore, the step of block 132 is only performed once for each morphological group 60 when the threshold size is first exceeded for the respective morphological group 60. In other embodiments, the step of block 132 may be performed when the size of the respective morphological groups 60 exceed various levels of thresholds. The step of block 132 may include the processing circuitry 41 being configured to select one of the heartbeat intervals of the set of activation signals 66 (e.g., pattern 62) most similar to other ones of the heartbeat intervals of the set of activation signals 66 (e.g., patterns 62) in that morphological group 60 as the new morphological template 64. The step of block 132 may include computing a correlation between all pairs of patterns 62 in that morphological group 60 using a suitable pattern matching correlation function, for example, as described with reference to FIG. 6, for every combination of patterns 62 in that morphological group 60. Each pattern 62 may be defined with its computed (pattern of interest) and compared against all other patterns 62 in that group 60. A variance is computed for the correlation of each pattern 62 with the rest of the patterns 62 in that morphological group 60, and then the pattern 62 with the minimum variance value is selected as the new morphological template 64 of that morphological group 60. The processing continues with the step of block 102 where a next pattern is processed.

The pattern matching process described above has been described as a live process which is performed as the activation signals 66 are received from the patient 28. In some embodiments, the pattern matching process may be performed offline as a batch process. It should be noted that the pattern matching process may be performed using any suitable pattern matching process, for example, by clustering or any grouping methodology.

The patterns 62 may be logically grouped using any suitable identification. For example, a database table may store respective annotation timestamps of the respective patterns 62 with identifications of the respective groups 60 in which the patterns 62 are grouped. The database table may then be queried to provide a count of the patterns 62 in each group 60, a most recent activation time of one of the patterns 62 in a group 60, sequences of the patterns 62 of the same group, and cycle length associated with patterns 62. The database table may also include fields for identifying the morphological template 64 of each morphological group 60, storing respective pattern of interests (POI) (described in more detail with reference to FIG. 5) of respective patterns 62, marking the morphological template 64 as favorites (described in more detail with reference to FIG. 7).

Figure 5:
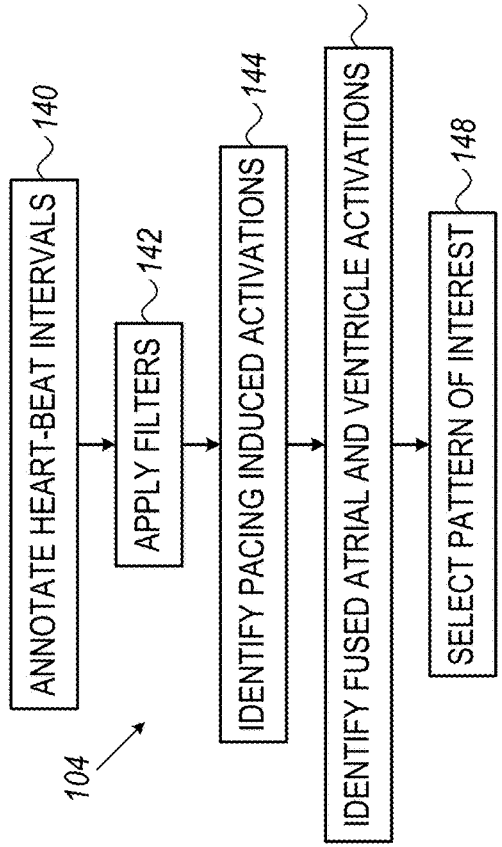

Reference is now made to FIG. 5, which is a flowchart describing sub-steps in the step of block 104 of FIG. 4.

The processing circuitry 41 is configured to annotate (block 140) the activation signals 66 generating timestamps which identify the locations of the relevant electrical activations in the activation signals 66. The activation signals 66 are therefore divided into intervals by the time stamps with each interval representing the electrical activity associated with a heartbeat.

Any suitable method of annotation may be used to provide annotation time stamps for the ECG or IEGM signals. An annotation of a signal is the assumed time of occurrence of the signal. In one embodiment the annotation corresponds to the time of occurrence of the largest positive value on one selected ECG signal. Several options exist for the reference annotation (positive value, negative value, largest negative slope, largest positive slope) and for IEGM signals, the time of occurrence typically corresponds to the time of activation of the section of myocardium generating the signal. Criteria for choosing the ECG signal for annotations, corresponding to that described above or other criteria, may be defined by physician.

Any suitable method of annotation may be used such as the method described in U.S. Pat. No. 8,700,136 to Rubinstein, which provides a method for processing a "raw" or filtered intracardiac signal, which may be unipolar or bipolar. Typically, the processing comprises fitting the intracardiac signal to a predetermined waveform, and deriving an annotation time of the signal from the fitted signal, rather than from the raw signal. Typically, a unipolar signal is fitted to an equation representative of a single complete oscillation, for example:

$$V_{unipolar}(t) = A \frac{((t-t_i)-t_s)}{e^{w(t-t_i)^2}} \qquad (1)$$

where $V_{unipolar}(t)$ represents the varying unipolar potential signal measured at the electrode at a time t; $t_i$ is a temporal displacement of the signal, with respect to the time t=0, $t_i$ corresponding to the time when an activation wave passes through the electrode position; A is an amplitude of the signal; $t_s$ is a parameter defining an asymmetry of the signal; and w is a parameter defining a width of the signal.

A bipolar signal may be fitted to an equation representative of a difference of two single complete oscillations, typically separated by a temporal difference. In some embodiments the single complete oscillation corresponds to a differential of a Gaussian function. An asymmetry factor may be applied to the differential, and in some embodiments the asymmetry factor corresponds to a Gaussian function. If the ECG signal is a bipolar signal, it may be assumed to be generated by the difference between a unipolar signal $V_{unipolar}(t)_1$ on one electrode and a unipolar signal $V_{unipolar}(t)_2$ on another electrode. For bipolar signals such as these the processor fits an equation (2), derived from equation (1), to the signal:

$$V_{bipolar}(t) = \qquad (2)$$

$$V_{unipolar}(t)_2 - V_{unipolar}(t)_1 = A_2 \frac{((t-t_{i2})-t_{S2})}{e^{w_2(t-t_{i2})^2}} - A_1 \frac{((t-t_{i1})-t_{S1})}{e^{w_1(t-t_{i1})^2}}$$

where $V_{bipolar}(t)$ represents the varying bipolar potential signal measured at the electrode at a time t; $V_{unipolar}(t)_1$, $V_{unipolar}(t)_2$, also termed $V_1$ and $V_2$, are as defined above for equation (1); $t_{i1}$, $t_{i2}$ are temporal displacements of $V_1$, $V_2$; $A_1$, $A_2$ are amplitudes of $V_1$, $V_2$; $t_{s1}$, $t_{s2}$ define asymmetries of $V_1$, $V_2$; and $w_1$, $w_2$ define widths of $V_1$, $V_2$. For a bipolar signal there is a temporal difference, $\Delta t_i = t_{i1} - t_{i2}$, equal to a difference between the temporal displacements of the two unipolar signals $V_{unipolar}(t)_1$ and $V_{unipolar}(t)_2$. The temporal difference between the two unipolar signals is typically a function of the spatial separation of the two electrodes generating the bipolar signal, and of an electrode orientation relative to a propagation direction of the activation wave. Thus, in the case of two electrodes, at least a component of the propagation direction of the activation wave may be determined from the temporal difference of the unipolar signals. It will be appreciated that for more than two electrodes, the temporal differences between the respective unipolar signals detected by the more than two electrodes, as well as the positions of the electrodes, typically allow multiple components of the propagation direction to be found. From the multiple components, the propagation direction (not just a component) of the activation wave may be estimated.

Other US Patents including U.S. Pat. Nos. 9,259,165, and 10,376,221 and US Patent Publication Nos. 2017/0042443 and 2019/0223808 describe alternative annotation techniques.

In some embodiments, the processing circuitry 41 is configured to filter (block 142) the activation signals 66 to remove noise and other artifacts. Noise is generally more of a problem with IEGM signals than with ECG signals.

For example, each unipolar signal of the IEGM signals may be sampled at 1 kHz after passing through a 250 Hz finite impulse response (FIR) lowpass filter (LPF). The additional filtering may be applied to remove the baseline wander, caused by patient movement and respiration.

A Median filter may be applied to the signal with a size of +/−20 milliseconds (ms). Sharp changes in the signal may be removed using an additional FIR filter that is applied on the Median filtered signal, padded with 20 zero samples (for example). Filter coefficients may be computed as follows:

$$FIRcoeff = \frac{0.5*(1-\mathrm{Cos}[2*\pi*x])}{\sum 0.5*(1-\mathrm{Cos}[2*\pi*x])} \text{ for } x \in \left\{0, 1 \text{ with steps of } \frac{1}{38}\right\}$$

The Median filtered signal is subtracted from the original signal, removing the baseline wander while preserving the signal morphology yielding a filtered signal as follows:

FilteredSignal=Signal−FIR(MedianFilteredSignal)

Any suitable filtering technique may be performed in addition to, or instead of, the above filtering.

Activations induced by pacing may be irrelevant to the pattern matching process and therefore the processing circuitry 41 is configured to identify (block 144) pacing induced beats and assign a suitable identification to the pacing induced beats to exclude then from the pattern matching process. Each incoming annotated heartbeat having an annotation time stamp (TS) may be tested for pacing inducement by the following steps:

A pacing segment may be defined as follow:

[Annotation TS−250 ms,Annotation TS+100 ms]

A Pacing Activation Signal may be computed for the signals 66 defined by the Pacing Segment while applying:

$$\text{Pacing Activation Signal} = \left|\frac{dv}{dt}\left(\sum \left|\frac{dv}{dt}\text{Pacing Segment}\right|\right)\right|$$

If the maximum value of the Pacing Activation Signal is above a Pacing Threshold, the beat is classified as pacing (e.g., '−1'), and the algorithm continues to the next beat. Otherwise, the algorithm continues to the next sub-step in the step of block 104. Example Pacing Threshold are as follows:

$$\text{Pacing Threshold} = \begin{cases} 0.25 \text{ mV} & ECG \text{ Signals} \\ 4 \text{ mV} & IEGM \text{ Signals} \end{cases}$$

IC signals may manifest activations from the Atrium and the Ventricle, which at times are overlapping in time. These fused activations have a different morphology caused by the waves' interference, and therefore are generally not used in the pattern matching and grouping described above with reference to FIG. 4. As such, the processing circuitry 41 may be configured to identify (block 146) these fused activations and assign a suitable identification to the fused activations to exclude then from the pattern matching process. Each incoming IC annotated beat may be tested for fused activation, by the proximity of the annotation to a BS activation annotation (on the precordial leads). If the IC annotation is found to be within 100 ms. from a ventricle activation identified from the BS activation signals 66, the IC annotation may be classified as fused, and the algorithm continues to process the next incoming beat.

The incoming patterns 62 may be compared to the morphological templates 64 based on a certain window around the annotation time stamp assigned to each pattern 62. In some embodiments, a pattern of interest (POI) may be defined to limit the extent of the patterns 62 for computing a correlation between patterns 62 and morphological template 64. In some embodiments, the POI may be computed for patterns 62 which become morphological template 64, but not for all patterns 62.

The processing circuitry 41 is configured to select (block 148) a POI. An Activity Segment may be defined around the reference annotation as follows:

[Annotation TS−150 ms,Annotation TS+150 ms]

An Activity Signal may be computed for the signals 66 defined by the Activity Segment by applying a Median Filter with a window (e.g., of 15 ms or any suitable value) as follows:

$$\text{Activity Signal} = MedianFilter\left(\sum \left|\frac{dv}{dt}\text{Activity Segment}\right|\right)$$

An Activity Threshold may be computed using the Activity Signal as follows:

Activity Threshold=(max(Activity Signal[$i_{101}$ to $i_{-101}$])−min(Activity Signal))+min(Activity Signal)

A local maximum may be computed to allocate the peak of the activity of the Activity Signal, 100 ms (for example) around the reference annotation:

Local Maximum=max(Activity Signal[$i_{101}$ to $i_{-101}$])

In the above two formulas, i is a sample point index and the signal is digitized and includes 1000 samples in a 1 KS/s signal.

A buffer of 10 ms (for example) may be computed around the points of intersection of the Activity Signal with the Activity Threshold, surrounding the Local Maximum, and the POI may be set as follows:

POI=[First intersection left to Local Maximum−10 ms,First intersection right to Local Maximum+ 10 ms]

Figure 6:
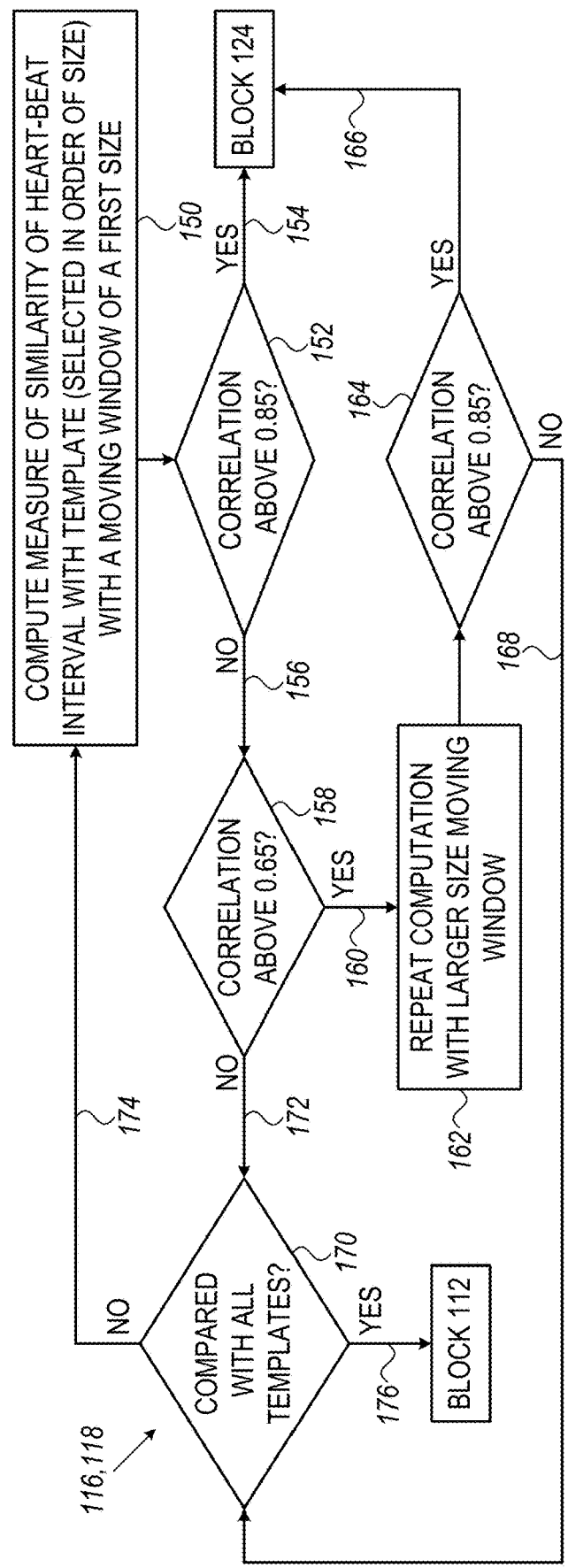

Reference is now made to FIG. 6, which is a flowchart including sub-steps of the steps of blocks 116, 118 of FIG. 4.

The processing circuitry 41 is configured to compute (block 150) the measure of similarity with the recently received heartbeat interval of the activation signals 66 (e.g., the recently received pattern 62) with one of the morphological templates 64. Comparison of the recently received heartbeat interval may be performed against the various morphological templates 64 according to a group size in which each template 64 is grouped, with the morphological template 64 of the largest group being selected first for comparison, and so on according to a decreasing group size. Therefore, the first morphological template 64 selected may be the morphological template 64 of the morphological group 60 containing the largest number of patterns 62.

The measure of similarity is computed between the recent received pattern 62 and the morphological template 64 using a moving window. In one embodiment, the moving window has a size of plus and minus 10 ms around the reference annotation, and the window is moved in increments of 1 ms. Any other suitable window size and increment size may be used.

The measure of similarity may be computed using any suitable correlation method, for example a Pearson Correlation or a weighted Pearson Correlation. An example of a weighted Pearson Correlation which may be used in embodiments of the present invention now follows.

The following description describes a correlation function for IC signals. A correlation function may utilize a weighting mechanism to compare each annotated incoming beat (e.g., pattern) against the (pre-defined POI) of the template 64. The correlation function may be defined as:

$$SignalCorr_i = \frac{TemplateSignal_i \cdot CandidateSignal_i}{\sqrt{TemplateSignal_i TemplateSignal_i} * NormSignal}$$

where $NormSignal = \sqrt{TemplateSig_i \cdot TemplateSig_i}$ if $0.1 \times TemplateSig_i \cdot TemplateSig_i > CandidateSig_i \cdot CandidateSig_i$ Otherwise, $NormSignal = \sqrt{CandidateSig_i \cdot CandidateSig_i}$ Weights may be applied to each of the channels that correspond to the respective unipolar IEGM signals 66 received from each electrode of a catheter. The channel weights are calculated based on the maximum slope of the template's signals, indicating the predominant channels which should have more effect on the final correlation outcome. Notably, the maximum slope of the template signals is the derivative function of the template signals such that the channel weights are derivates of the template slopes. By using the derivative based function, sharp activations may be distinguishable from shallow activations which may provide a better template match as compared to an amplitude-based function which may provide more inconclusive results for certain activations. For example, the channel weights of each of the channels may be calculated based on:

$$W_i = \frac{maxSlope_i}{\sum maxSlope_i}$$

wherein:

maxSlope$_i$=Min(maxThreshold,Max(differences(SignalCorr$_i$)))

The maxThreshold may be defined as a predefined value (e.g., 0.2).

A single correlation value for all the channels may be determined. The integrative correlation value may be calculated by:

Corr=Σ$W_i$*SignalCorr$_i$.

Correlation of body surface ECG signals may be performed according to a method described in U.S. Pat. No. 10,433,749 to Nakar, et al., which describes performing a cross-correlation between the initial set and the subsequent set, so as to generate a correlation coefficient that is a measure of a goodness of fit between geometries of the initial set and the subsequent set. In particular, the processing circuitry 41 computes for each ECG channel, (ECG i,j), where i is a numerical index defining the channel of the pattern 62 (typically, for BS ECG, i=1, 2, . . . 12), and j is a numerical index defining a position of an annotation of the ECG signal, for a current heartbeat interval associated with an annotation j, a correlation coefficient according to the following equation:

$$Correlation(x, y) = \frac{\sum_k (x - \bar{x})(y - \bar{y})}{\sqrt{\sum_k (x - \bar{x})^2 (y - \bar{y})^2}} \quad (3)$$

where, x is the sample value of the template 64 ECG data, $\bar{x}$ is the average value of the template 64 ECG data, y is the sample value of the current heartbeat interval ECG data being tested, $\bar{y}$ is the average value of the current heartbeat interval ECG data being tested, and k is a numerical index defining which data sample of the ECG signal is being analyzed. For example, if the POI is for 120 ms, from −50 ms (before the reference annotation) to +70 ms (after the reference annotation), and we sample every ms, then k is a set of 120 values for the 120 samples.

It will be understood that the correlation performed by equation (3) compares the geometries, or shapes, of the template 64 ECG data with the current heartbeat interval ECG data. A high value of Correlation (x,y), i.e., close to unity, means that the two geometries, of the template 64 and of the current heartbeat, are similar.

In another step of the algorithm, the processing circuitry 41 computes an overall correlation, for a specific heartbeat interval, using the values of the correlation coefficient calculated using equation 3. The processing circuitry 41 computes an absolute maximum amplitude $A_{i,j}$ of the ECG signal being tested for the current heartbeat interval, and an absolute maximum amplitude Bi of the corresponding ECG signal in the morphological template 64. The processor uses the sum of $A_{i,j}$ and Bi as weights to calculate an overall correlation according to equation (4).

$$\text{Overall Correlation} = \frac{\sum_{i=1}^{N}(A_{i,j} + B_i)\text{Corr}_{i,j}}{\sum_{i=1}^{N}(A_{i,j} + B_i)} \quad (4)$$

Where $\text{Corr}_{i,j}$ is the correlation coefficient calculated by equation (3), and N is the number of ECG channels being analyzed. In the case of BS signals, N is typically 12.

The overall correlation coefficient calculated by equation (4) depends on the phase of the ECG signal being tested relative to the phase of the morphological template 64. In a further step, the processing circuitry 41 iteratively changes the phase, of the ECG signal being tested, relative to the phase of the morphology pattern and the computations described above with reference to equations (3) and (4) are repeated according to each new relative phase to compute the overall correlation for each of the relative phases.

At a decision block 152, the processing circuitry 41 is configured to check if the measure of similarity (e.g., correlation) is above 0.85. The value 0.85 is given by way of example only and any other suitable threshold value may be used. If the measure of similarity is above 0.85 (branch 154), processing continues with the step of block 124 of FIG. 4 in which the currently received pattern 62 is added to the matching morphological group 60. If the measure of similarity is not above 0.85 (branch 156) the processing continues at a decision block 158 at which the processing circuitry 41 is configured to check if the measure of similarity is above 0.65. The value 0.65 is given by way of example only and any other suitable threshold value may be used. If the measure of similarity is above 0.65 (branch 160), the processing circuitry 41 is configured to repeat (block 162) the computation of the measure of similarity with a larger sliding window, for example, plus and minus 40 ms around the reference annotation, and the window is moved in increments of 1 ms. The use of a larger sliding window (e.g., plus or minus 40 ms) may be computationally heavy and therefore it is generally used for a correlation in an uncertain range, e.g., between 0.65 and 0.85. The steps of blocks 158 and 162 provide an optimization mechanism having consideration for the computation challenge of such a large data set. Any suitable window size and increment size may be used. At a decision block 164, the processing circuitry 41 is configured to check if the computed measure of similarity is above 0.85. If the measure of similarity is above 0.85 (branch 166), processing continues with the step of block 124 of FIG. 4 in which the currently received pattern 62 is added to the matching morphological group 60. If the measure of similarity is not above 0.85 (branch 168) processing continues at a decision block 170. Similarly, if at the decision block 158 it was found that the measure of similarity was not above 0.65 (branch 172), processing continues at the decision block 170. At decision block 170, the processing circuitry 41 is configured to check if the currently received pattern 62 has been compared to all the templates 64. If the currently received pattern 62 has not been compared to all the morphological templates 64 (branch 174), the step of block 150 is repeated for the currently received pattern 62 and another one of the morphological templates 64. The template 64 to be used is typically selected from the remaining morphological templates 64 (i.e., not already used as a comparison with the currently received pattern 62) of the largest group 60 (i.e. the largest number of patterns 62 in the group). If the currently received pattern 62 has already been compared to all the morphological template 64 (branch 176), the step of block 112 of FIG. 4 is performed in which the currently received pattern 62 becomes a new morphological template 64 for a new morphological group 60.

Figure 7:
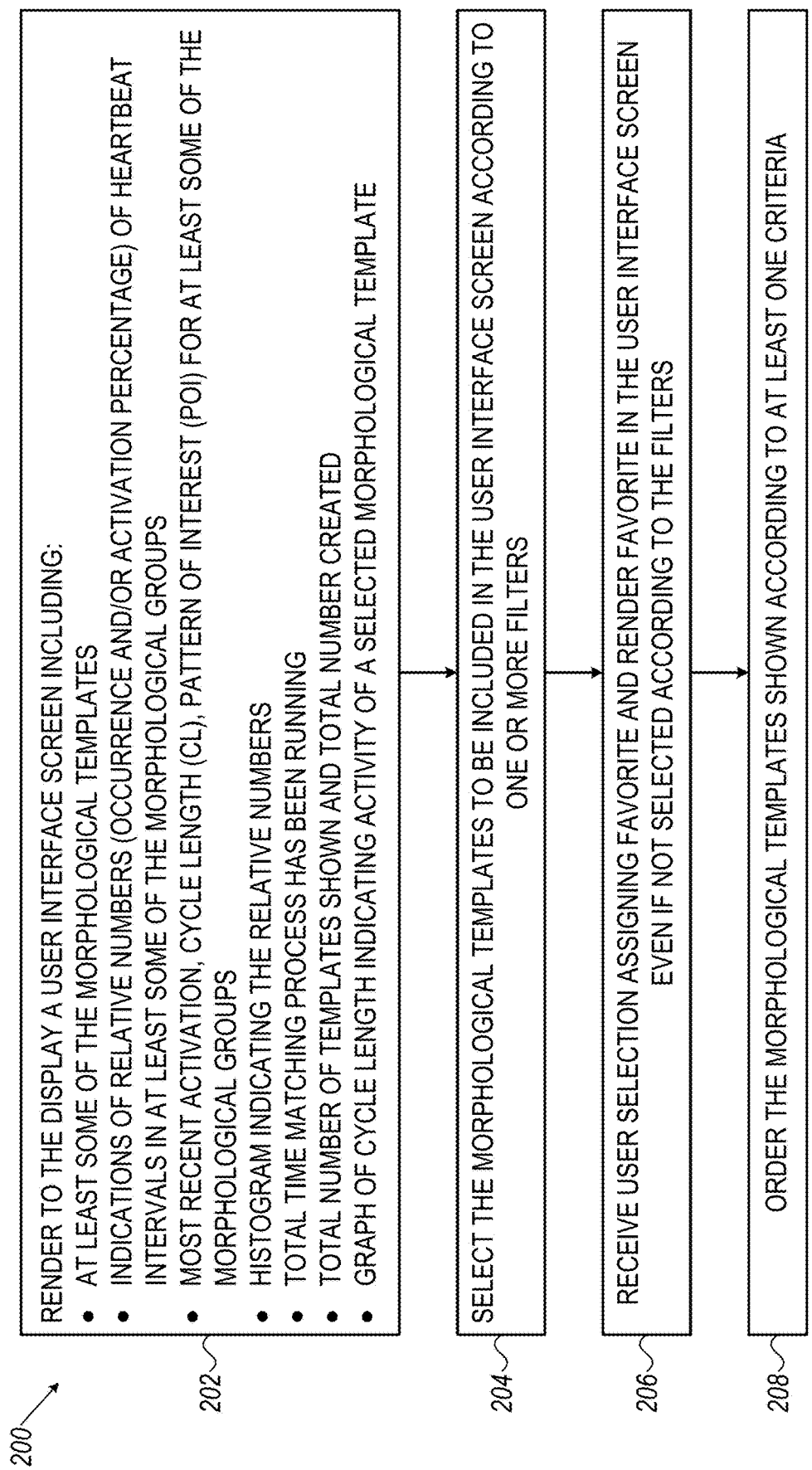
Figure 8:
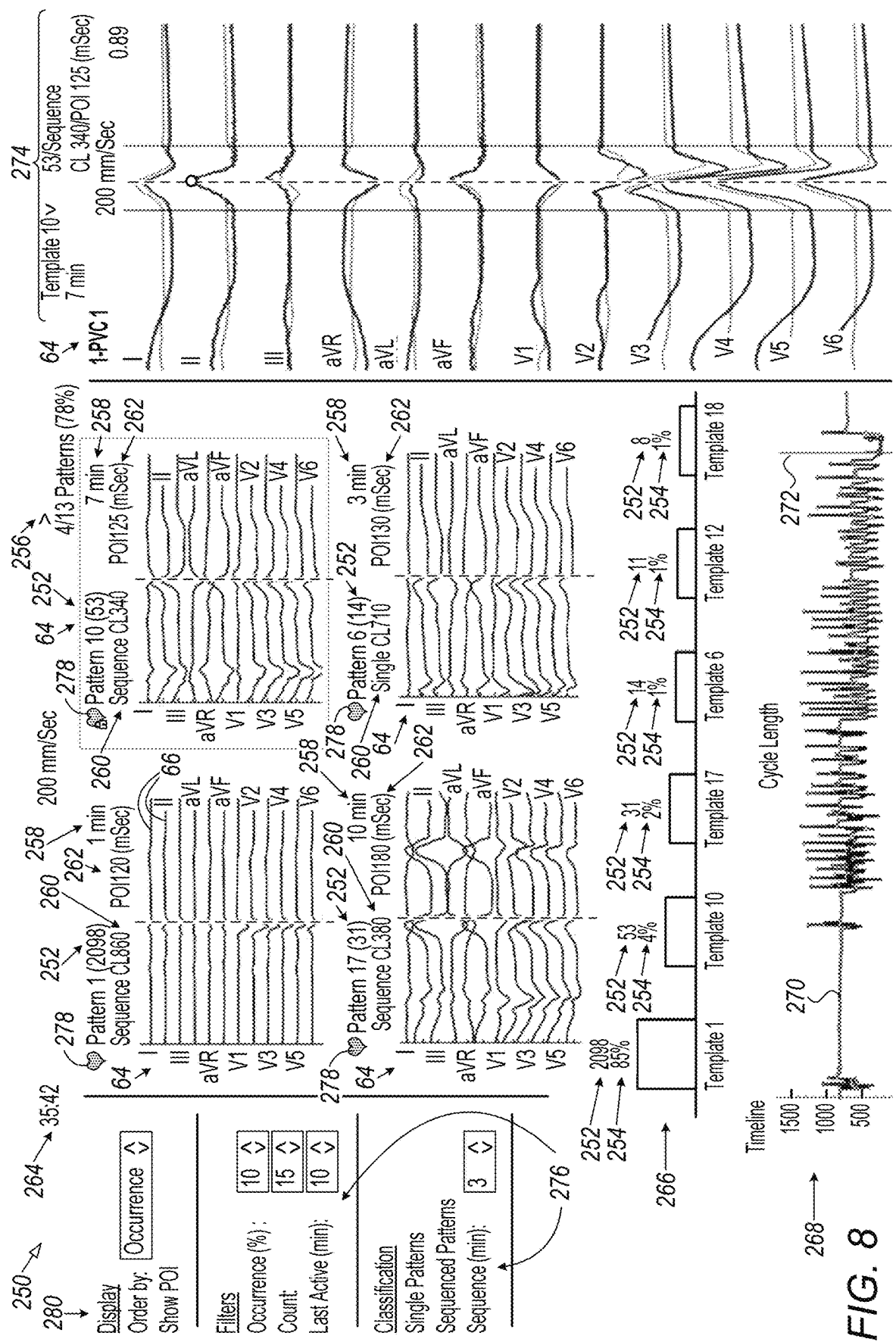
FIG. 8 is a schematic view of a user interface screen generated by the system of FIG. 1.

Reference is now made to FIG. 7, which is a flowchart 200 including steps in rendering a user interface screen 250 in the system 20. Reference is also made to FIG. 8, which is a schematic view of the user interface screen 250 generated by the system 20 of FIG. 1.

The processing circuitry 41 is configured to render (block 202) to the display 27 (FIG. 1) the user interface screen 250 including respective morphological templates 64 and indications of respective relative numbers of heartbeat intervals of the set of activation signals 66 (e.g., the patterns 62) in the respective morphological groups 60 (FIG. 3). The indication may include a count 252 and/or an activation percentage 254 (or occurrence rate) of the heartbeat intervals of the set of activation signals 66 in the respective morphological groups 60. In other words, the indication may include the count 252 and/or activation percentage 254 (or occurrence rate) of the patterns 62 in the morphological groups 60 of the respective displayed morphological templates 64. The activation percentage 254 (or occurrence rate) may be expressed as the percentage (or other fraction) of patterns 62 in one of the morphological groups 60 out of the total count of patterns 62 (in all the morphological groups 60). The morphological templates 64 of all the morphological groups 60, or only some of the groups 60 may be selected for display in the user interface screen 250. Criteria to select which morphological templates 64 are shown, and their order, are discussed in more detail below. If there is not enough room on the user interface screen 250 for all the selected morphological templates 64 to be shown at the same time, the morphological templates 64 may be shown on different scrollable pages indicated by a page selector 256.

The user interface screen 250 may also include a most recent activation time 258 for each of the displayed morphological templates 64 (i.e., when the morphology represented by the respective morphological template 64 was last active), a cycle length 260 associated with the displayed morphological templates 64, and a POI 262 associated with the displayed morphological templates 64. The user interface screen 250 may also show a total time 264 that the pattern matching process has been running.

The indications of respective relative numbers of heartbeat intervals of the set of activation signals 66 (e.g., the patterns 62) may include a histogram 266 indicating the respective relative numbers (e.g., the counts 252 and the activation percentages 254 or occurrence rates) of the heartbeat intervals of the set of activation signals 66 in the respective displayed morphological groups 60.

The processing circuitry 41 may also be configured to render the user interface screen 250 including a graph 268 of cardiac cycle length against time. The graph may indicate when a morphology of a selected morphological group 60 (or for multiple selected groups 60) was active by using different colors on a cycle length line 270 (shown in FIG. 8 using different grey scales). A vertical line 272 may be used to indicate when a selected morphology was active.

One of the morphological templates 64 (e.g., Pattern/Template 10) may be selected and shown in a larger pane 274 (on the right side of the user interface screen 250) so that the physician 30 may inspect the selected morphological template 64 in more detail and compare its correlation with the real-time ECG or IEGM currently being captured.

As discussed above, filters 276 may be used to determine which of the morphological templates 64 are displayed based on filtering criteria. The filter bar may be displayed all the time or only when opened by a user. Therefore, the processing circuitry 41 is configured to select (block 204) respective ones of the morphological templates 64 to be included in the user interface screen 250 from the available morphological templates 64 according to any one or more of the following filters: a minimum count of the heartbeat intervals of the set of activation signals 66 (e.g. patterns 62) in the respective morphological groups 64 (so that groups 60 with a count below this value are excluded); a minimum activation percentage (or occurrence rate) of the heartbeat intervals of the set of activation signals 66 in the respective morphological groups 64 (so that groups 60 with a percentage activation below this value are excluded); a last activation of the heartbeat intervals of the set of activation signals 66 in the respective ones of the morphological groups 60 (so that morphologies only active earlier than this time are excluded).

Additionally, or alternatively, a classification filter may be used which may provide the physician 30 with details regarding the type of activation mechanism by differentiating between a number of consecutive activations with the same morphology (e.g., VT, flutter, etc.) from a single abnormal activation with a normal rhythm sequence (e.g., PVC, PAC, etc.). The classification filter may define a minimum consecutive sequence of heartbeat intervals in a same one of the morphological groups (which could be set to any size sequence or could be set to even include single patterns).

A heart symbol 278 associated with each displayed morphological template 64 may be selected to make that morphological template 64 a favorite so that the morphological template 64 will be displayed in the user interface screen 250 irrespective of the selected filters. Therefore, the processing circuitry 41 is configured to receive (block 206) a user selection assigning a favorite of the morphological templates 64 (e.g., Pattern 10 in FIG. 8), and render the favorite in the user interface screen 250 even if the favorite is not selected according to the one or more filters 276. The heart symbol 278 associated with Pattern 10 in FIG. 8 is shown with a padlock symbol indicating that Pattern 10 has been selected as a favorite and has also been assigned to a specific map as a pattern matching filter.

The selected morphological template 64 may be ordered in the user interface screen 250 according to any suitable display order criteria 280. The processing circuitry 41 is configured to order (block 208) the respective morphological templates 64 in the user interface screen 250 according to any one or more of the following: a count of the heartbeat intervals of the set of activation signals 66 in the respective morphological groups 60; an activation percentage (or occurrence rate) of the heartbeat intervals of the set of activation signals 66 in the respective morphological groups 60; an earliest activation of the heartbeat intervals of the set of activation signals 66 in the respective morphological groups 60; or a latest activation of the heartbeat intervals of the set of activation signals 66 in the respective morphological groups 60. The physician 30 may start, stop, or pause the automatic pattern matching process at will.

Figure 9:
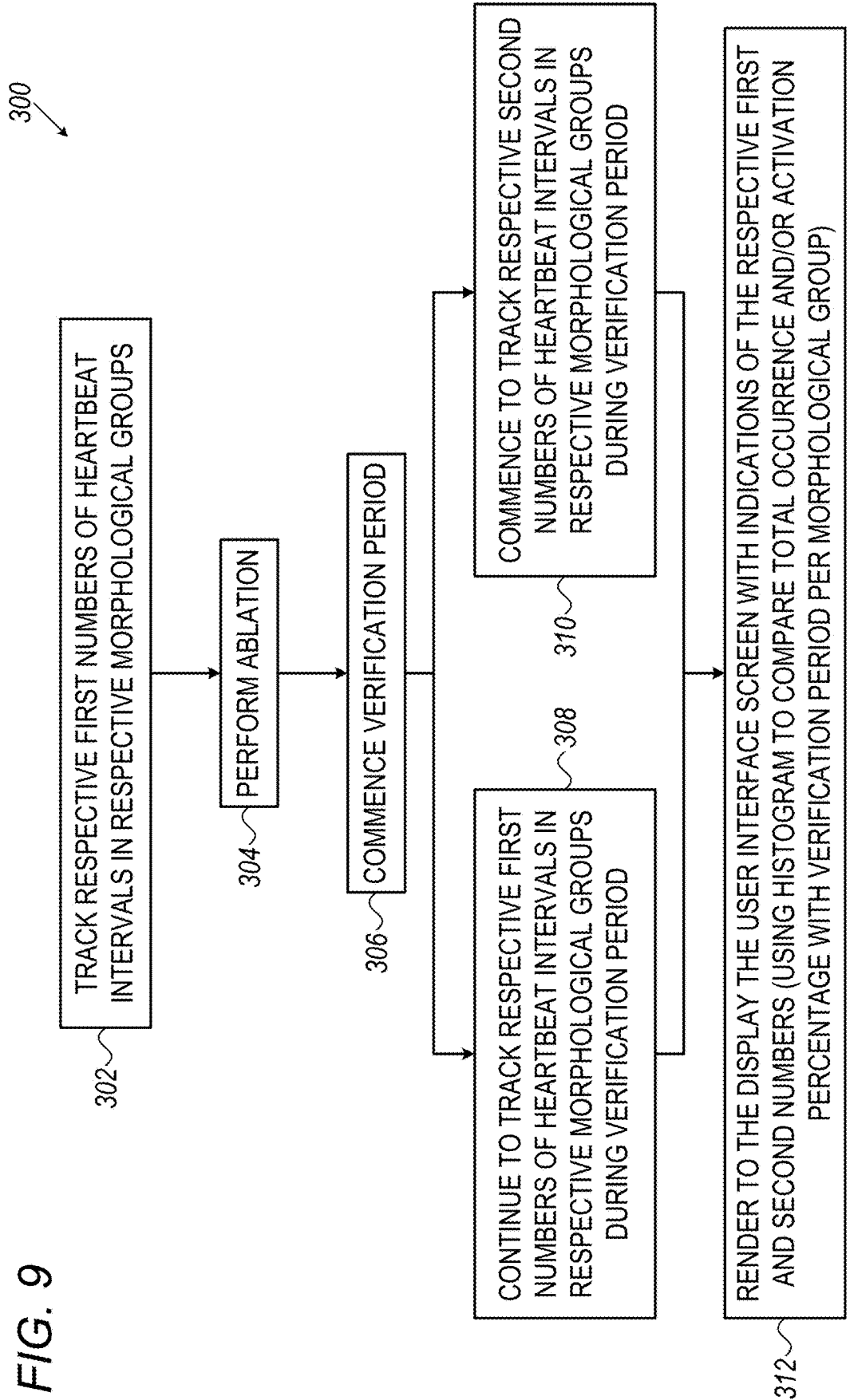
FIG. 9 is a flowchart including steps in a method of operation of the system of FIG. 1.
Figure 10:
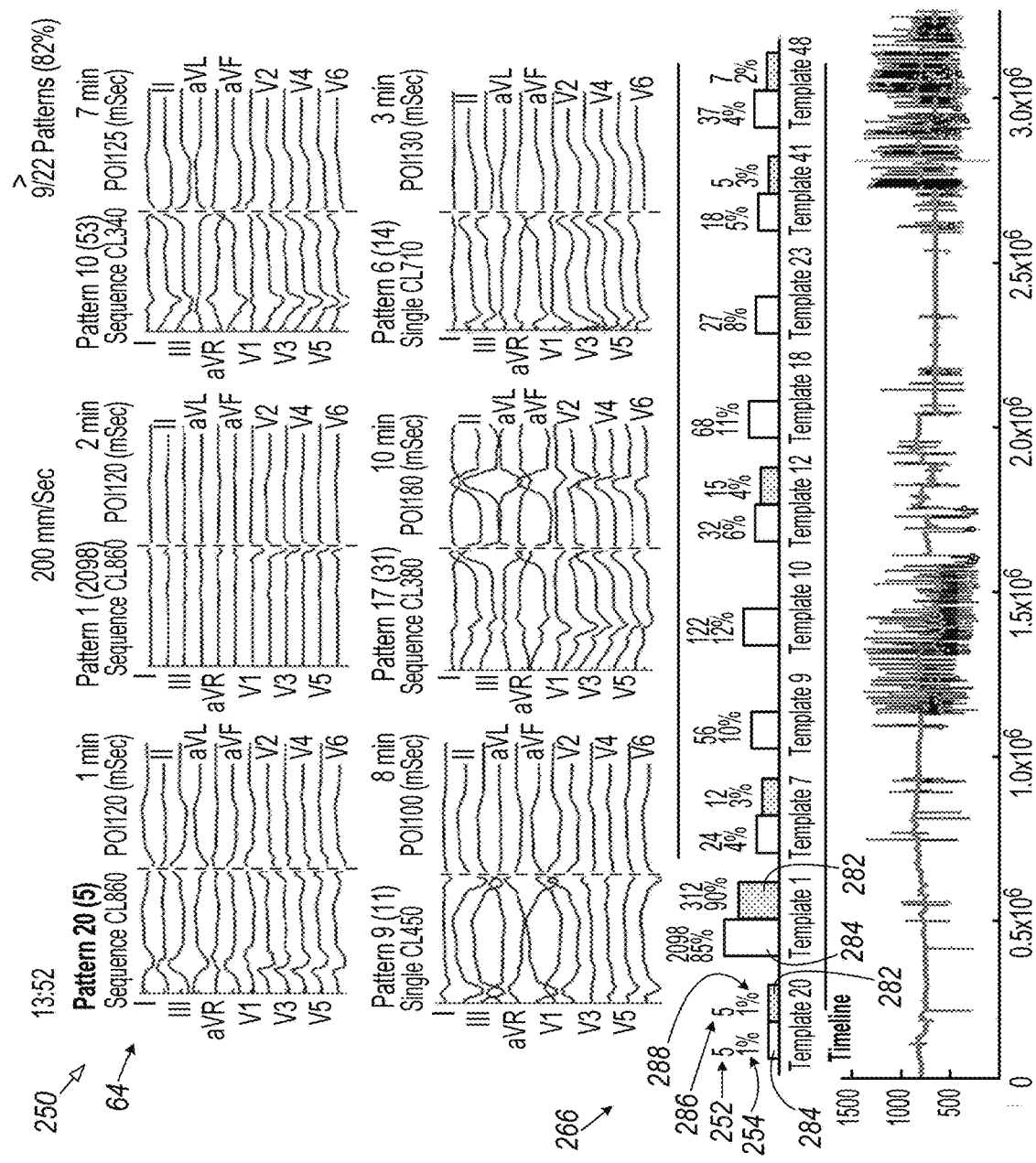
FIG. 10 is a schematic view of the user interface screen of FIG. 8 in a verification mode.

Reference is now made to FIGS. 9 and 10. FIG. 9 is a flowchart 300 including steps in a method of operation of the system 20 of FIG. 1. FIG. 10 is a schematic view of the user interface screen 250 of FIG. 8 in a verification mode.

The physician 30 may want to see the effect that a particular procedure or therapy has on the patterns 62 produced by the heart 26 (FIG. 1) of the patient 28 (FIG. 1). For example, after an ablation procedure, the physician 30 may want to see if problematic arrhythmias associated with a certain morphological template 64 or morphological templates 64 have stopped or subsided. In order to track the effectiveness of the procedure, secondary bars 282 (only some labeled for the sake of simplicity) may be added to the histogram 266 in addition to primary bars 284 (only some labeled for the sake of simplicity). The primary bars 284 indicate the count 252 (only one labeled for the sake of simplicity) and/or activation percentage 254 (or occurrence rate) (only one labeled for the sake of simplicity) of the respective morphological groups 60 represented by the primary bars 284 from when the pattern matching process was initiated (prior to the procedure or therapy, e.g., ablation). The secondary bars 282, which are respectively disposed next to the primary bars 284, indicate a count 286 (only one labeled for the sake of simplicity) and/or an activation percentage 288 (or occurrence rate) (only one labeled for the sake of simplicity) of the respective morphological groups 60 only during the verification period (e.g., from after the procedure or therapy, e.g., ablation).

Template 20 shows an equal number in the primary bar 284 as in the secondary bar 282 as template 20 initially appeared during the verification period and may represent a morphology which has changed due to the therapy (e.g., the ablation). Templates 9, 10, 18 and 20 do not include a secondary bar indicating that the morphology associated with these templates is not being exhibited during the verification period.

The processing circuitry 41 (FIG. 1) is configured to track (block 302) first respective numbers of heartbeat intervals of the set of activation signals 66 added to the respective morphological groups 60 prior to a verification period. The system 20 is configured to perform (block 304) an ablation procedure. The processing circuitry 41 is configured to commence (block 306) the verification period responsively to receiving a user input. The processing circuitry 41 is configured to continue to track (block 308) the first respective numbers of heartbeat intervals of the set of activation signals 66 added to the respective morphological groups 60 during the verification period. The processing circuitry 41 is configured to track (block 310) second respective numbers of heartbeat intervals of the set of activation signals added to the respective morphological only during the verification period. The processing circuitry 41 is configured to render (block 312) to the display 27 the user interface screen 250, which simultaneously includes indications of the first respective numbers (e.g., the counts 252 and activation percentages 254 or occurrence rates) and the second respective numbers (e.g., the counts 286 and the activation percentages 288 or occurrence rates) of heartbeat intervals added to the respective morphological groups 60.

The processing circuitry 41 is configured to emphasize (e.g., using highlighting and/or bolding and/or any other suitable formatting change) a new morphological template 64 (e.g., Template/Pattern 20) first created during the verification period. The new morphological template 64 is typically treated like a favorite morphological template 64 in that the new morphological template 64 remains on the user interface screen 250 irrespective of the selected filters and optionally irrespective of the preferred display order so that the new morphological template 64 will receive appropriate attention of the physician 30.

Reference is again made to FIG. 8. FIG. 8 shows that the activation count 252 of heartbeat intervals in each of the respective morphological groups 60 (FIG. 3) of patterns 10, 17, and 6 is below 60. Therefore, it may be difficult to successfully generate a meaningful electro-anatomical map, e.g., a local activation time (LAT) map, for any of the morphological groups 60 of patterns 10, 17, and 6. However, the physician 30 may want to identify the source of the arrhythmia associated with any of the patterns 10, 17, and 6 and to perform an ablation at the source of the arrhythmia. Pacing may be used to help identify the source of the arrhythmia of such patterns in order for the physician 30 to ablate the source of the arrhythmia, as described in more detail with reference to FIG. 11 below.

It should be noted that the count limit of 60 is used by way of example only. The count limit may be set above 60 or below 60 regarding the usefulness of using the captured heartbeat intervals to generate a meaningful electro-anatomic map. The limit may depend on the methods used to generate the electro-anatomic map and/or the skill of the physician 30 (FIG. 1).

Figure 11:
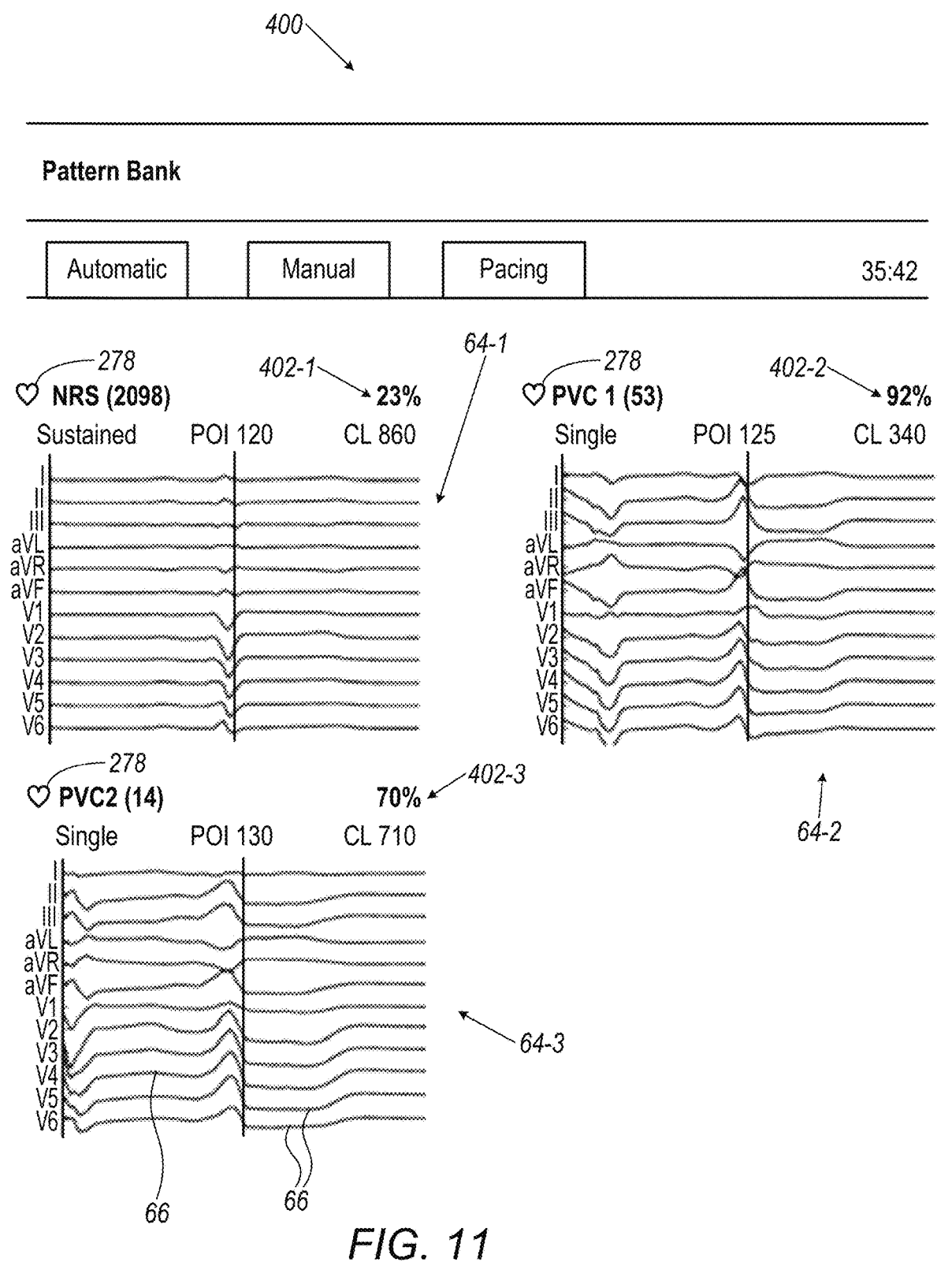

Reference is now made to FIG. 11, which is a schematic view of a pacing user interface screen 400 generated by the system 20 of FIG. 1. As described above with reference to FIG. 5, activations induced by pacing may be irrelevant to the pattern matching process and therefore the processing circuitry 41 (FIG. 1) is generally configured to identify (in block 144 of FIG. 5) pacing induced beats and assign a suitable identification to the pacing induced beats to exclude then from the pattern matching process.

In some embodiments, although the pacing induced beats are generally not added as patterns 62 (FIG. 3) to any of the morphological groups 60 (FIG. 3), the pacing induced beats are compared to the morphological templates 64 (FIG. 3) to determine measures of similarity 402 (e.g., correlations) with the respective morphological templates 64. The measures of similarity 402 to the respective morphological template 64 may be displayed in real-time so that the physician 30 (FIG. 1) may determine the source of arrhythmia based on the displayed measures of similarity 402. For example, the catheter 40 is moved around the heart chamber, and when the catheter 40 (FIG. 1) is disposed at a certain location in a chamber of the heart 26 (FIG. 1) the measure of similarity 402 to one of the morphological templates 64 is greater than 90% (for example), which is a good indication that the catheter 40 is disposed close to the source of the arrhythmia associated with that morphological template 64. The percentage threshold defining a good indication is determined by the physician 30 and may be any suitable value or percentage. For example, the percentage threshold defining a good indication may be less than, or greater than, 90%. The catheter 40 may be moved around the chamber of the heart until the physician 30 is satisfied that the source of the arrhythmia associated with one of the morphological templates 64 (of interest to the physician 30) has been found based on the measure of similarity 402 to that morphological template 64 exceeding a certain measure of similarity.

FIG. 11 shows three morphological templates 64, namely a morphological template 64-1 for Normal Sinus Rhythm (NSR), a morphological template 64-2 for Premature Ventricular Complex (PVC) 1, and a morphological template 64-3 for PVC 2. A measure of similarity 402 is displayed adjacent to each morphological template 64. For example, a measure of similarity 402-1 equal to 23% is displayed adjacent to the morphological template 64-1 for NSR, a measure of similarity 402-2 equal to 92% is displayed adjacent to the morphological template 64-2 for PVC 1, and a measure of similarity 402-3 equal to 70% is displayed adjacent to the morphological template 64-3 for PVC 2. Therefore, it appears that the catheter 40 is disposed in the chamber of the heart 26 close to the source of the arrhythmia associated with PVC 1. Therefore, based on the above analysis, the physician 30 may decide to ablate at the present location of the catheter 40 associated with the source of the arrhythmia associated with PVC 1.

Therefore, in some embodiments, the processing circuitry 41 (FIG. 1) is configured to compute respective measures of similarity 402 between a pacing induced heartbeat interval of the set of activation signals 66 (only some labeled for the sake of simplicity) and respective ones of the previously assigned morphological template 64 of respective morphological groups 60. The pacing induced heartbeat interval of the set of activation signals 66 may be compared to some or all of the previously assigned morphological template 64. For example, the pacing induced heartbeat interval of the set of activation signals 66 may be compared to the morphological templates 64 marked as a favorite (e.g., using the heart symbol 278).

The processing circuitry 41 is configured to render to the display 27 (FIG. 1) the pacing user interface screen 400 including indications of the respective measures of similarity 402 between the pacing induced heartbeat interval of the set of activation signals 66 and the respective previously assigned morphological templates 64 of the respective morphological groups 60. Some of the computed measures of similarity 402 may be displayed on the pacing user interface screen 400 and some of the computed measures of similarity 402 may be displayed on a different user interface screen or not displayed at all. In some embodiments, all of the computed measures of similarity 402 are displayed on the pacing user interface screen 400. In some embodiments, the processing circuitry 41 is configured to render to the display 27 the user interface screen 400 including the respective previously assigned morphological templates 64 and indications of the respective measures of similarity 402 between the pacing induced heartbeat interval of the set of activation signals 66 and the respective previously assigned morphological templates 64 of the respective morphological groups 60. Subsequent pacing induced heartbeats may be captured and detected and processed by the processing circuitry 41 to compute and render the measures of similarity 402 on the pacing user interface screen 400.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A medical system utilizing automatic pattern acquisition, the system comprising:

respective electrodes configured for application to a body of a subject and configured to output a set of respective activation signals in response to electrical activity of a heart of the subject captured over a sequence of heartbeat intervals; and a processor configured to:

classify a first heartbeat interval of the set of activation signals as a first morphological template;

for a second heartbeat interval following the first heartbeat interval: compute a measure of similarity between the second heartbeat interval of the set of activation signals and the first morphological template; group the second heartbeat interval of the set of activation signals in a first morphological group with the first morphological template responsively to the measure of similarity exceeding a predefined threshold; and classify the second heartbeat interval of the set of activation signals as a second morphological template responsively to the measure of similarity not exceeding the predefined threshold; and for a subsequent heartbeat interval: compute a first measure of similarity between the subsequent heartbeat interval of the set of activation signals and at least one of a plurality of previously assigned morphological templates of respective morphological groups, wherein the first measure of similarity between the subsequent heartbeat interval and the at least one of the plurality of previously assigned morphological templates is computed within a moving window of a first duration; if the first measure of similarity is above a first correlation threshold but less than a second correlation threshold, compute a second measure of similarity between the subsequent heartbeat interval of the set of activation signals and at least one of a plurality of previously assigned morphological group within a second a moving window of a second duration greater than the first duration; group the subsequent heartbeat interval of the set of activation signals in one of the morphological groups of one of the previously assigned morphological templates responsively to the measure of similarity with the one previously assigned morphological template exceeding the second threshold; and classify the subsequent heartbeat interval of the set of activation signals as another morphological template responsively to the measure of similarity with the previously assigned morphological templates not exceeding the first threshold.

2. The system according to claim 1, wherein the processor is configured to find a new morphological template for one of the morphological groups responsively to a number of heartbeat intervals of the set of activation signals in the one morphological group exceeding a given threshold size.

3. The system according to claim 2, wherein the processor is configured to select one of the heartbeat intervals of the set of activation signals most similar to other ones of the heartbeat intervals of the set of activation signals in the one morphological group as the new morphological template.

4. The system according to claim 1, further comprising a display, wherein the processor is configured to render to the display a user interface screen including respective ones of the morphological templates and indications of respective relative numbers of heartbeat intervals of the set of activation signals in respective ones of the morphological groups.

5. The system according to claim 4, wherein the indication includes a histogram indicating the respective relative numbers of the heartbeat intervals of the set of activation signals in the respective ones of the morphological groups.

6. The system according to claim 4, wherein the indication includes a count and/or an activation percentage and/or an occurrence rate of the heartbeat intervals of the set of activation signals in the respective ones of the morphological groups.

7. The system according to claim 4, wherein the processor is configured to order the respective ones of the morphological templates in the user interface screen according to any one or more of the following: a count of the heartbeat intervals of the set of activation signals in the respective ones of the morphological groups; an activation percentage or an occurrence rate of the heartbeat intervals of the set of activation signals in the respective ones of the morphological groups; an earliest activation of the heartbeat intervals of the set of activation signals in the respective ones of the morphological groups; or a latest activation of the heartbeat intervals of the set of activation signals in the respective ones of the morphological groups.

8. The system according to claim 4, wherein the processor is configured to select the respective ones of the morphological templates included in the user interface screen from the morphological templates according to any one or more of the following filters: a minimum count of the heartbeat intervals of the set of activation signals in the respective ones of the morphological groups; a minimum activation percentage or an occurrence rate of the heartbeat intervals of the set of activation signals in the respective ones of the morphological groups; a last activation of the heartbeat intervals of the set of activation signals in the respective ones of the morphological groups; a minimum consecutive sequence of heartbeat intervals in a same one of the morphological groups.

9. The system according to claim 8, wherein the processor is configured to receive a user selection assigning a favorite of the morphological templates, the processor being configured to render the favorite in the user interface screen even if the favorite is not selected according to the one or more filters.

10. The system according to claim 4, wherein:

the processor is configured to separately track:

first respective numbers of heartbeat intervals of the set of activation signals added to the respective morphological groups prior to, and during, a verification period; and second respective numbers of heartbeat intervals of the set of activation signals added to the respective morphological groups during the verification period; and the processor is configured to render to the display the user interface screen, which simultaneously includes indications of the first respective numbers and the second respective numbers of heartbeat intervals added to the respective morphological groups.

11. The system according to claim 10, wherein the processor is configured to emphasize a new morphological template created during the verification period.

12. The system according to claim 4, wherein the processor is configured to render the user interface screen including a graph of cardiac cycle length against time, the graph indicating when a morphology of a selected one of the morphological groups was active.

13. The system according to claim 1, further comprising a display, wherein the processor is configured to:
    compute respective measures of similarity between a pacing induced heartbeat interval of the set of activation signals and respective ones of the previously assigned morphological templates of respective morphological groups; and
    render to the display a user interface screen including indications of the respective measures of similarity between the pacing induced heartbeat interval of the set of activation signals and the respective previously assigned morphological templates of the respective morphological groups.

14. The system according to claim 13, wherein the processor is configured to render to the display the user interface screen including the respective previously assigned morphological templates and the indications of the respective measures of similarity between the pacing induced heartbeat interval of the set of activation signals and the respective previously assigned morphological templates of the respective morphological groups.

\* \* \* \* \*